United States Patent
Satou et al.

(10) Patent No.: US 11,407,708 B2
(45) Date of Patent: Aug. 9, 2022

(54) ACTIVE ESTER COMPOUND AND COMPOSITION AND CURED PRODUCT OBTAINED USING THE SAME

(71) Applicant: DIC Corporation, Tokyo (JP)

(72) Inventors: Yutaka Satou, Ichihara (JP); Kazuhisa Yamoto, Ichihara (JP)

(73) Assignee: DIC Corporation, Tokyo (JP)

( * ) Notice: Subject to any disclaimer, the term of this patent is extended or adjusted under 35 U.S.C. 154(b) by 129 days.

(21) Appl. No.: 16/623,444

(22) PCT Filed: Apr. 24, 2018

(86) PCT No.: PCT/JP2018/016547
§ 371 (c)(1),
(2) Date: Dec. 17, 2019

(87) PCT Pub. No.: WO2018/235424
PCT Pub. Date: Dec. 27, 2018

(65) Prior Publication Data
US 2020/0207700 A1    Jul. 2, 2020

(30) Foreign Application Priority Data

Jun. 21, 2017  (JP) .............................. JP2017-121335

(51) Int. Cl.
| C07C 69/76 | (2006.01) |
| C08G 59/42 | (2006.01) |
| H01L 23/29 | (2006.01) |
| H05K 1/03 | (2006.01) |

(52) U.S. Cl.
CPC .......... C07C 69/76 (2013.01); C08G 59/4223 (2013.01); H01L 23/295 (2013.01); H05K 1/0373 (2013.01)

(58) Field of Classification Search
CPC ... C07C 69/76; C08G 59/4223; H01L 23/295; H05K 1/0373
USPC ....................................................... 528/88
See application file for complete search history.

(56) References Cited

U.S. PATENT DOCUMENTS

| 4,035,559 | A | 7/1977 | Fujii et al. |
| 4,037,034 | A | 7/1977 | Plank |
| 7,019,104 | B1 | 3/2006 | Okada et al. |
| 2002/0151731 | A1* | 10/2002 | Pews ................... C07F 9/65502 |
| | | | 549/549 |
| 2005/0012070 | A1 | 1/2005 | Inoue et al. |
| 2010/0272670 | A1 | 10/2010 | Uhrich et al. |
| 2015/0099820 | A1 | 4/2015 | Seo et al. |

FOREIGN PATENT DOCUMENTS

| CN | 106700073 A | 5/2017 |
| EP | 0376370 A1 | 7/1990 |
| EP | 0 489 691 A2 | 6/1992 |
| JP | 51-143634 A | 12/1976 |
| JP | H02-212560 A | 8/1990 |
| JP | 5-9236 A | 1/1993 |
| JP | 11-349666 A | 12/1999 |
| JP | 2004-189715 A | 7/2004 |
| JP | 2015-522085 A | 8/2015 |
| JP | 2016-108437 A | 6/2016 |
| JP | 2016-156019 A | 9/2016 |
| JP | 2017-88544 A | 5/2017 |
| WO | 01/32749 A1 | 5/2001 |

OTHER PUBLICATIONS

International Search Report dated Jul. 24, 2018, issued for PCT/JP2018/016547.
CAS Registry 680574-28-1 dated May 7, 2004.
Wan et al. "A novel biobased epoxy resin with high mechanical stiffness and low flammability: synthesis, characterization and properties", Journal of Materials Chemistry A: Materials for Energy and Sustainability, 2015,3(43), pp. 21907-21921.
Chemical Abstracts Index No. 955941-82-9; STN Entry Date Nov. 26, 2007.
Chemical Abstracts Index No. 908029-20-9; STN Entry Date Sep. 20, 2006.
Chemical Abstracts Index No. 761432-05-7; STN Entry Date Oct. 13, 2004.
Chemical Abstracts Index No. 61682-67-5; STN Entry Date Nov. 16, 1984.
Chemical Abstracts Index No. 2897-56-5; STN Entry Date Nov. 16, 1984.
Chemical Abstracts Index No. 61682-66-4; STN Entry Date Nov. 16, 1984.
Chemical Abstracts Index No. 331973-14-9; STN Entry Date Apr. 20, 2001.
Chemical Abstracts Index No. 1147180-60-6; STN Entry Date May 18, 2009.
Chemical Abstracts Index No. 1072434-29-7; STN Entry Date Nov. 13, 2008.

(Continued)

Primary Examiner — David T Karst
(74) Attorney, Agent, or Firm — Locke Lord LLP; James E. Armstrong, IV; Nicholas J. DiCeglie, Jr.

(57) ABSTRACT

The present invention aims to provide a means by which a cured product to be obtained has a low dielectric loss tangent and higher heat resistance. Specifically, provided are an active ester compound represented by chemical formula (1):

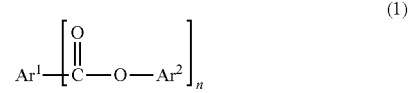

(where in chemical formula (1), $Ar^1$ is a substituted or unsubstituted first aromatic ring group, and each $Ar^2$ is independently a substituted or unsubstituted second aromatic ring group, in which at least one of $Ar^1$ and $Ar^2$ has an unsaturated bond-containing substituent, and n is an integer of 2 or 3), a curable composition containing the active ester compound, and a cured product thereof.

9 Claims, No Drawings

(56) References Cited

OTHER PUBLICATIONS

Chemical Abstracts Index No. 510717-67-6; STN Entry Date May 5, 2003.
Chemical Abstracts Index No. 505050-26-0; STN Entry Date Apr. 25, 2003.
Chemical Abstracts Index No. 470668-94-1; STN Entry Date Nov. 6, 2002.
Chemical Abstracts Index No. 352638-40-5; STN Entry Date Aug. 26, 2001.
Chemical Abstracts Index No. 334498-59-8; STN Entry Date May 3, 2001.
Chemical Abstracts Index No. 331973-17-2; STN Entry Date Apr. 20, 2001.
Chemical Abstracts Index No. 331973-16-1; STN Entry Date Apr. 20, 2001.
Chemical Abstracts Index No. 331973-15-0; STN Entry Date Apr. 20, 2001.
Chemical Abstracts Index No. 144095-61-4; STN Entry Date Oct. 23, 1992.
Chemical Abstracts Index No. 132721-06-3; STN Entry Date Mar. 22, 1991.
Chemical Abstracts Index No. 144095-60-3; STN Entry Date Oct. 23, 1992.

* cited by examiner

ACTIVE ESTER COMPOUND AND COMPOSITION AND CURED PRODUCT OBTAINED USING THE SAME

TECHNICAL FIELD

The present invention relates to an active ester compound and a composition and a cured product obtained using the active ester compound.

BACKGROUND ART

In recent years, electronic devices have been reduced in size and increased in performance, and accordingly, various materials used have been required to have higher performance. For example, in semiconductor package substrates, higher speeds and higher frequencies of signals are used, and materials having low electrical energy losses, i.e., low dielectric loss tangents, are required.

As such a material having a low dielectric loss tangent, for example, PTL 1 describes an invention relating to a resin composition containing (A) an epoxy resin, (B) an active ester compound, (C) a smear-suppressing component, and (D) an inorganic filler. In this case, the resin composition is characterized in that predetermined amounts of the active ester compound (B), the smear-suppressing component (C), and the inorganic filler (D) are contained based on 100% by mass of a non-volatile component in the resin composition and that the smear-suppressing component (C) is formed of rubber particles.

PTL 1 states that a cured product obtained from the resin composition can achieve a low dielectric loss tangent. It is also stated that a smear (resin residue) in a via hole can be suppressed after the cured product is subjected to drilling processing and then roughing treatment.

It is also stated that the active ester compound (B) described in PTL 1 is a compound having one or more active ester groups in one molecule and can reduce the dielectric loss tangent of the cured product of the resin composition.

CITATION LIST

Patent Literature

PTL 1: Japanese Unexamined Patent Application Publication No. 2016-156019

SUMMARY OF INVENTION

Technical Problem

PTL 1 states that the use of the active ester compound or the like can reduce the dielectric loss tangent of the resulting cured product. However, it has been found that such a cured product may not always have sufficient heat resistance.

Accordingly, it is an object of the present invention to provide a means by which a cured product to be obtained has a low dielectric loss tangent and higher heat resistance.

Solution to Problem

The inventors have conducted intensive studies to solve the foregoing problems and have found that the foregoing problems can be solved by the use of a predetermined active ester compound. This finding has led to the completion of the present invention.

The present invention relates to an active ester compound represented by chemical formula (1):

[Chem. 1]

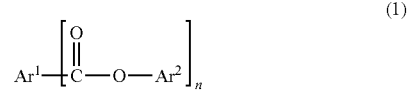

where in chemical formula (1), $Ar^1$ is a substituted or unsubstituted first aromatic ring group, and each $Ar^2$ is independently a substituted or unsubstituted second aromatic ring group, in which at least one of $Ar^1$ and $Ar^2$ has an unsaturated bond-containing substituent, and n is an integer of 2 or 3.

Advantageous Effects of Invention

According to the present invention, there is provided the active ester compound from which a cured product to be obtained has a low dielectric loss tangent and higher heat resistance.

DESCRIPTION OF EMBODIMENTS

Embodiments for carrying out the present invention will be described in detail below.

<Active Ester Compound>

An active ester compound according to an embodiment is represented by chemical formula (1) below.

[Chem. 2]

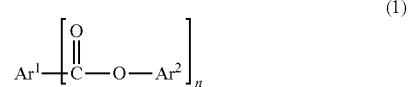

The use of the active ester compound represented by chemical formula (1) can provide a cured product having a low dielectric loss tangent and higher heat resistance. Although the reason for this is not entirely clear, this is presumably due to the following reasons.

The ester bond of the active ester compound according to the embodiment connects two aromatic rings and has high reactivity with an epoxy group of an epoxy resin described below. The high reactivity can prevent or inhibit the formation of a hydroxy group due to the ring-opening of the epoxy group.

The active ester compound according to the embodiment has no or substantially no hydroxy group in its molecule. Thus, no or substantially no hydroxy group originating from the active ester compound is contained in a cured product obtained by the reaction of the active ester compound according to the embodiment.

Thus, in the case of the active ester compound according to the embodiment, it is possible to prevent or inhibit the formation of a hydroxy group at the time of curing. In general, hydroxy groups, which have high polarity, are known to increase the dielectric loss tangent. The use of the active ester compound according to the embodiment enables a cured product to have a low dielectric loss tangent.

The active ester compound according to the embodiment has two or three each having reactivity with an epoxy group of an epoxy resin described below. This enables a cured product to have a higher cross-linking density to improve the heat resistance.

The active ester compound according to the embodiment has at least one unsaturated bond-containing substituent. This results in the formation of a cross-link based on the unsaturated bond-containing substituent as well as a cross-link based on an epoxy group and an ester bond, thereby enabling the achievement of a higher cross-linking density.

That is, because the active ester compound according to the embodiment has the unsaturated bond-containing substituent, a cured product to be obtained can have higher heat resistance.

Surprisingly, the presence of the unsaturated bond-containing substituent can reduce the dielectric loss tangent of a cured product to be obtained. Such an effect is presumed to be due to the fact that, for example, the presence of the unsaturated bond-containing substituent results in the resulting cured product having a low polarity in its entirety to reduce the loss of electrical energy.

Preferably, the active ester compound is a liquid at ordinary temperature (25° C.) or has a melting point in the range of 40° C. to 200° C., from the viewpoint of achieving better handleability when adjusted as a composition described below, and a better balance between the heat resistance and the dielectric properties of a cured product thereof.

In chemical formula (1), $Ar^1$ is a substituted or unsubstituted first aromatic ring group and preferably has 3 to 30 carbon atoms. As described below, n in chemical formula (1) is an integer of 2 or 3. Thus, two or three hydrogen atoms of the aromatic ring in the first aromatic ring group are substituted with "—C(O)OAr$^2$".

Examples of the first aromatic ring group include, but are not particularly limited to, groups in which two or three hydrogen atoms are removed from an aromatic compound, such as groups in which two or three hydrogen atoms are removed from a monocyclic aromatic compound, e.g., benzene, furan, pyrrole, thiophene, imidazole, pyrazole, oxazole, isoxazole, thiazole, isothiazole, pyridine, pyrimidine, pyridazine, pyrazine, or triazine; and groups in which two or three hydrogen atoms are removed from a fused aromatic compound, e.g., naphthalene, anthracene, phenalene, phenanthrene, quinoline, isoquinoline, quinazoline, phthalazine, pteridine, coumarin, indole, benzimidazole, benzofuran, or acridine. Additionally, the first aromatic ring group may be a combination of a plurality of these aromatic compounds. Examples thereof include groups in which two or three hydrogen atoms are removed from an aromatic ring assembly compound, such as biphenyl, binaphthalene, bipyridine, bithiophene, phenylpyridine, phenylthiophene, terphenyl, diphenylthiophene, or quaterphenyl; and groups in which two or three hydrogen atoms are removed from an aromatic compound, such as diphenylmethane, diphenylethane, 1,1-diphenylethane, 2,2-diphenylpropane, naphthylphenylmethane, triphenylmethane, dinaphthylmethane, dinaphthylpropane, phenylpyridylmethane, fluorene, or diphenylcyclopentane, linked by an alkylene.

The first aromatic ring group represented by $Ar^1$ may have a substituent. In this case, the "substituent on the first aromatic ring group" is a substituent replaced with at least one hydrogen atom on the aromatic ring in the first aromatic ring group. Specific examples of the substituent on the first aromatic ring group include, but are not particularly limited to, an alkyl group having 1 to 10 carbon atoms, an alkoxy group having 1 to 10 carbon atoms, an alkyloxycarbonyl group having 2 to 15 carbon atoms, an alkylcarbonyloxy group having 2 to 15 carbon atoms, and a halogen atom.

Examples of the alkyl group having 1 to 10 carbon atoms include, but are not particularly limited to, a methyl group, an ethyl group, a propyl group, an isopropyl group, a n-butyl group, an isobutyl group, a sec-butyl group, a tert-butyl group, a n-pentyl group, an isopentyl group, a tert-pentyl group, a neopentyl group, a 1,2-dimethylpropyl group, a n-hexyl group, an isohexyl group, a n-nonyl group, a cyclopropyl group, a cyclobutyl group, a cyclopentyl group, a cyclohexyl group, a cycloheptyl group, a cyclooctyl group, and a cyclononyl group.

Examples of the alkoxy group having 1 to 10 carbon atoms include, but are not particularly limited to, a methoxy group, an ethoxy group, a propoxy group, an isopropoxy group, a butoxy group, a pentyloxy group, a hexyloxy group, a 2-ethylhexyloxy group, an octyloxy group, and a nonyloxy group.

Examples of the alkyloxycarbonyl group having 2 to 15 carbon atoms include, but are not particularly limited to, a methyloxycarbonyl group, an ethyloxycarbonyl group, a propyloxycarbonyl group, an isopropyloxycarbonyl group, a butyloxycarbonyl group, a n-butyloxycarbonyl group, an isobutyloxycarbonyl group, a sec-butyloxycarbonyl group, and a tert-butyloxycarbonyl group.

Examples of the alkylcarbonyloxy group having 2 to 15 carbon atoms include, but are not particularly limited to, a methylcarbonyloxy group, an ethylcarbonyloxy group, a propylcarbonyloxy group, an isopropylcarbonyloxy group, a butylcarbonyloxy group, a n-butylcarbonyloxy group, an isobutylcarbonyloxy group, a sec-butylcarbonyloxy group, and a tert-butylcarbonyloxy group.

Examples of the halogen atom include a fluorine atom, a chlorine atom, a bromine atom, and an iodine atom.

Among those described above, $Ar^1$ is preferably a substituted or unsubstituted first aromatic hydrocarbon group having 6 to 30 carbon atoms. When $Ar^1$ is the first aromatic hydrocarbon group, an increase in dielectric loss tangent due to lone-pair electrons can be prevented or inhibited, and a cured product to be obtained can have a lower dielectric loss tangent, which is preferred. In the present specification, the "first aromatic hydrocarbon group" refers to an aromatic hydrocarbon group consisting of carbon atoms and hydrogen atoms among the first aromatic ring groups.

Examples of the first aromatic hydrocarbon group include groups in which two or three hydrogen atoms are removed from an aromatic hydrocarbon compound, such as groups in which two or three hydrogen atoms are removed from benzene, naphthalene, anthracene, phenalene, or phenanthrene. Additionally, the first aromatic hydrocarbon group may be a combination of a plurality of these aromatic hydrocarbon compounds. Examples thereof include groups in which two or three hydrogen atoms are removed from an aromatic ring assembly compound, such as biphenyl, binaphthalene, terphenyl, or quaterphenyl, and groups in which two or three hydrogen atoms are removed from an aromatic hydrocarbon compound, such as diphenylmethane, diphenylethane, 1,1-diphenylethane, 2,2-diphenylpropane, naphthylphenylmethane, triphenylmethane, dinaphthylmethane, dinaphthylpropane, fluorene, or diphenylcyclopentane, linked by an alkylene.

The first aromatic hydrocarbon group represented by $Ar^1$ may have a substituent. In this case, the "substituent on the first aromatic hydrocarbon group" refers to a substituent replaced with at least one hydrogen atom on the aromatic ring in the first aromatic hydrocarbon group. The substituent on the aromatic hydrocarbon group can be composed of a carbon atom and a hydrogen atom. A specific example of the substituent on the aromatic hydrocarbon group is, but not particularly limited to, an alkyl group having 1 to 10 carbon atoms. Examples of the alkyl group having 1 to 10 carbon atoms include those described above. The first aromatic hydrocarbon group may have one or a combination of two or more of the substituents described above.

Among those described above, $Ar^1$ is more preferably a group in which two or three hydrogen atoms are removed from benzene, toluene, o-xylene, m-xylene, p-xylene, naphthalene, 1-methylnaphthalene, 2-methylnaphthalene, 1,5-dimethylnaphthalene, 2,6-dimethylnaphthalene, 2,7-dimethylnaphthalene, or 2,3,6,7-, even more preferably a group in which two or three hydrogen atoms are removed from benzene, toluene, naphthalene, 1-methylnaphthalene, or 2-methylnaphthalene, particularly preferably a group in which two or three hydrogen atoms are removed from benzene or naphthalene, most preferably a group in which two or three hydrogen atoms are removed from benzene.

In an embodiment, $Ar^1$ may have an unsaturated bond-containing substituent. The unsaturated bond-containing substituent is a functional group containing an unsaturated bond and preferably having 2 to 30 carbon atoms.

Specific examples of the unsaturated bond-containing substituent include an alkenyl group having 2 to 30 carbon atoms and an alkynyl group having 2 to 30 carbon atoms.

Examples of the alkenyl group having 2 to 30 carbon atoms include, but are not particularly limited to, a vinyl group, an allyl group, a propenyl group, an isopropenyl group, a 1-propenyl group, a 1-butenyl group, a 2-butenyl group, a 3-butenyl group, a 1-hexenyl group, a 2-hexenyl group, a 3-hexenyl group, a 4-hexenyl group, a 5-hexenyl group, a 1-octenyl group, a 2-octenyl group, a 1-undecenyl group, a 1-pentaundecenyl group, a 3-pentadecenyl group, a 7-pentadecenyl group, a 1-octadecenyl group, a 2-octadecenyl group, a cyclopentenyl group, a cyclohexenyl group, a cyclooctenyl group, a 1,3-butadienyl group, a 1,4-butadienyl group, a hexa-1,3-dienyl group, a hexa-2,5-dienyl group, a pentadeca-4,7-dienyl group, a hexa-1,3,5-trienyl group, and a pentadeca-1,4,7-trienyl group.

Examples of the alkynyl group having 2 to 30 carbon atoms include, but are not particularly limited to an ethynyl group, a propargyl group, a 1-butynyl group, a 2-butynyl group, a 3-butynyl group, a 3-pentynyl group, a 4-pentynyl group, and a 1,3-butadiynyl group.

Examples of a preferred structure of $Ar^1$ include those represented by formulae (2-1) to (2-17) below.

[Chem. 3]

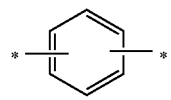

(2-1)

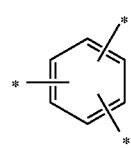

(2-2)

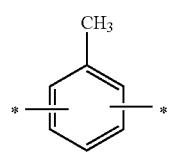

(2-3)

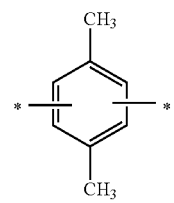

(2-4)

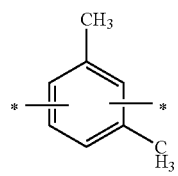

(2-5)

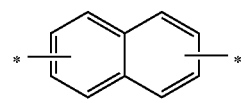

(2-6)

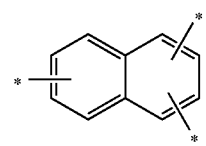

(2-7)

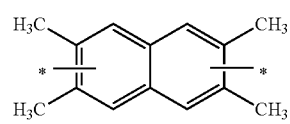

(2-8)

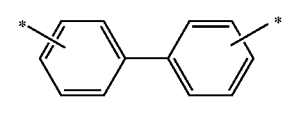

(2-9)

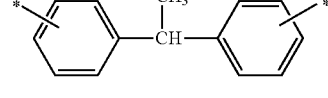

(2-10)

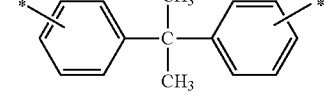

(2-11)

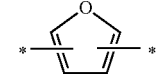

(2-12)

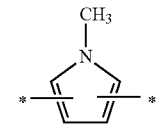

(2-13)

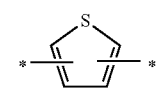

(2-14)

(2-15)

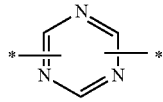 (2-16)

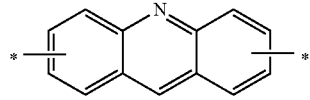 (2-17)

In formulae (2-1) to (2-17), each "*" represents a position that binds to "—C(O)OAr²". Each "-*" may be attached at any position on the aromatic ring.

Among these, formulae (2-1) to (2-11) are preferred. Formulae (2-1), (2-2), (2-6), (2-7), and (2-9) are more preferred. Formulae (2-1), (2-2), (2-6), and (2-7) are even more preferred. From the viewpoint of achieving high handleability and low viscosity of aromatic ester compound (A-1), (2-1) and (2-2) are preferred. From the viewpoint of enabling the resulting cured product to have higher heat resistance and a good balance with low dielectric properties, (2-6) and (2-7) are preferred.

At least one hydrogen atom on the aromatic ring in each of formulae (2-1) to (2-17) may be replaced with an unsaturated bond-containing group.

Preferably, each $Ar^2$ is independently a substituted or unsubstituted second aromatic ring group and preferably has 3 to 30 carbon atoms. As is clear from the description of chemical formula (1), one hydrogen atom on the aromatic ring in the second aromatic ring group is replaced with "—OC(O)Ar¹".

Examples of the second aromatic ring group include, but are not particularly limited to, a group in which one hydrogen atom is removed from an aromatic compound, such as a group in which one hydrogen atom is removed from a monocyclic aromatic compound, e.g., benzene, furan, pyrrole, thiophene, imidazole, pyrazole, oxazole, isoxazole, thiazole, isothiazole, pyridine, pyrimidine, pyridazine, pyrazine, or triazine, and a group in which one hydrogen atom is removed from a fused aromatic compound, e.g., naphthalene, anthracene, phenalene, phenanthrene, quinoline, isoquinoline, quinazoline, phthalazine, pteridine, coumarin, indole, benzimidazole, benzofuran, or acridine. Additionally, the second aromatic ring group may be a combination of a plurality of these aromatic compounds. Examples thereof include a group in which one hydrogen atom is removed from an aromatic ring assembly compound, such as biphenyl, binaphthalene, bipyridine, bithiophene, phenylpyridine, phenylthiophene, terphenyl, diphenylthiophene, or quaterphenyl, and a group in which one hydrogen atom is removed from an aromatic compound, such as diphenylmethane, diphenylethane, 1,1-diphenylethane, 2,2-diphenylpropane, naphthylphenylmethane, triphenylmethane, dinaphthylmethane, dinaphthylpropane, phenylpyridylmethane, fluorene, or diphenylcyclopentane, linked by an alkylene.

Among these, because a cured product having better dielectric properties is obtained, $Ar^2$ is preferably a substituted or unsubstituted benzene ring or naphthalene ring. From the viewpoint of achieving high handleability and low viscosity of the active ester compound, a benzene ring is preferred. From the viewpoint of enabling the resulting cured product to have higher heat resistance and a good balance with low dielectric properties, a naphthalene ring is preferred.

The second aromatic ring group represented by $Ar^2$ may have a substituent. In this case, the "substituent on the second aromatic ring" is a substituent replaced with at least one hydrogen atom on the aromatic ring in the second aromatic ring group. Specific examples of the substituent on the second aromatic ring group include, but are not particularly limited to, an alkyl group having 1 to 10 carbon atoms, an alkoxy group having 1 to 10 carbon atoms, an alkyloxycarbonyl group having 2 to 15 carbon atoms, an alkylcarbonyloxy group having 2 to 15 carbon atoms, and a halogen atom. In this case, examples of the alkyl group having 1 to 10 carbon atoms, the alkoxy group having 1 to 10 carbon atoms, the alkyloxycarbonyl group having 2 to 15 carbon atoms, the alkylcarbonyloxy group having 2 to 15 carbon atoms, and the halogen atom include those described above.

Among those described above, $Ar^2$ is preferably a substituted or unsubstituted second aromatic hydrocarbon group having 6 to 30 carbon atoms. When $Ar^2$ is the second aromatic hydrocarbon group, an increase in dielectric constant due to lone-pair electrons can be prevented or inhibited, and a cured product to be obtained can have a lower dielectric loss tangent, which is preferred. In the present specification, the "second aromatic hydrocarbon group" refers to an aromatic hydrocarbon group consisting of carbon atoms and hydrogen atoms among the second aromatic ring groups.

An example of the second aromatic hydrocarbon group is a group in which one hydrogen atom is removed from an aromatic hydrocarbon compound, such as benzene, naphthalene, anthracene, phenalene, or phenanthrene. Additionally, the second aromatic hydrocarbon group may be a combination of a plurality of these aromatic compounds. Examples thereof include a group in which one hydrogen atom is removed from an aromatic ring assembly compound, such as biphenyl, binaphthalene, terphenyl, or quaterphenyl; and a group in which one hydrogen atom is removed from an aromatic hydrocarbon compound, such as diphenylmethane, diphenylethane, 1,1-diphenylethane, 2,2-diphenylpropane, naphthylphenylmethane, triphenylmethane, dinaphthylmethane, dinaphthylpropane, fluorene, or diphenylcyclopentane, linked by an alkylene.

The second aromatic hydrocarbon group represented by $Ar^2$ may have a substituent. In this case, the "substituent on the second aromatic hydrocarbon group" is a substituent replaced with at least one hydrogen atom on the aromatic ring in the second aromatic hydrocarbon group. The substituent on the aromatic hydrocarbon group can be composed of a carbon atom and a hydrogen atom. A specific example of the substituent on the aromatic hydrocarbon group is, but not particularly limited to, an alkyl group having 1 to 10 carbon atoms. Examples of the alkyl group having 1 to 10 carbon atoms include those described above. The second aromatic hydrocarbon group may have one or a combination of two or more of the substituents described above.

Among those described above, $Ar^2$ is more preferably a group in which one hydroxy atom is removed from benzene, toluene, o-xylene, m-xylene, p-xylene, naphthalene, 1-methylnaphthalene, 2-methylnaphthalene, 1,5-dimethylnaphthalene, 2,6-dimethylnaphthalene, 2,7-dimethylnaphthalene, or 2,3,6,7-, even more preferably a group in which one hydroxy atom is removed from benzene, toluene, naphthalene, 1-methylnaphthalene, or 2-methylnaphthalene, particularly preferably a group in which one hydroxy atom is removed from benzene or naphthalene, most preferably a group in which one hydroxy atom is removed from benzene.

In an embodiment, $Ar^2$ may have the unsaturated bond-containing substituent described above. In this case, one unsaturated bond-containing substituent may be contained. Alternatively, two or more unsaturated bond-containing substituents may be contained.

Examples of a preferred structure of $Ar^2$ include those represented by formulae (3-1) to (3-17).

[Chem. 4]

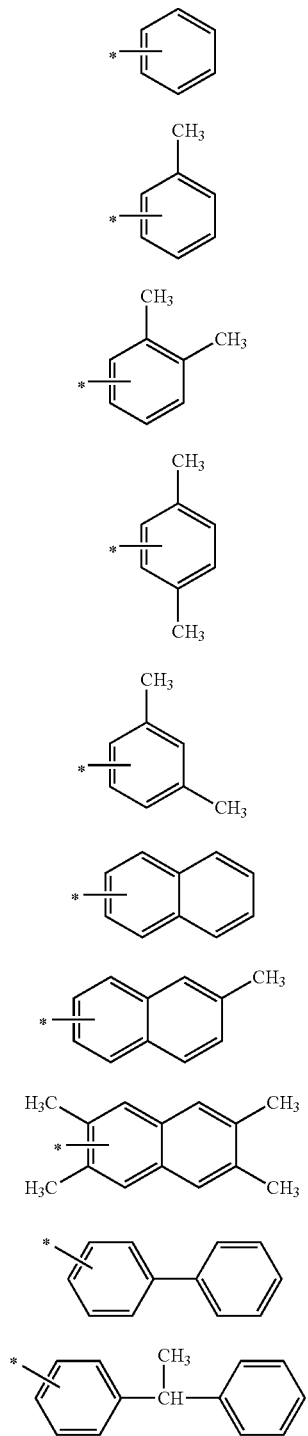

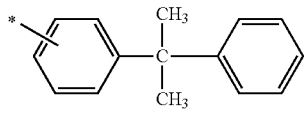

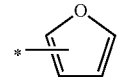

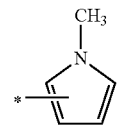

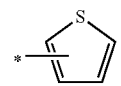

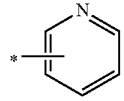

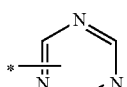

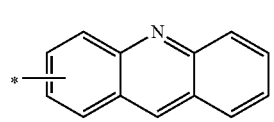

In formulae (3-1) to (3-17), each "*" represents a position that binds to "—OC(O)Ar¹". Each "-*" may be attached at any position on the aromatic ring.

Among these, formulae (3-1) to (3-11) are preferred. Formulae (3-1), (3-6), and (3-9) are more preferred. Formulae (3-1) and (3-6) are even more preferred.

At least one hydrogen atom on the aromatic ring in each of formulae (3-1) to (3-17) may be replaced with an unsaturated bond-containing group.

In chemical formula (1), at least one of $Ar^1$ and $Ar^2$ has an alkenyl group having 2 to 30 carbon atoms, which is an unsaturated bond-containing substituent. That is, only $Ar^1$ may have an unsaturated bond-containing substituent, only $Ar^2$ may have an unsaturated bond-containing substituent, or both $Ar^1$ and $Ar^2$ may have unsaturated bond-containing substituents.

In an embodiment, preferably, at least one of the $Ar^2$ groups has an unsaturated bond-containing substituent. More preferably, each $Ar^2$ has an unsaturated bond-containing substituent. It is even more preferred that $Ar^1$ have no unsaturated bond-containing substituent and each $Ar^2$ have an unsaturated bond-containing substituent. The presence of the unsaturated bond-containing substituent on $Ar^2$ results in a better balance between the heat resistance and the dielectric loss tangent of a cured product and is thus preferred.

In an embodiment, the unsaturated bond-containing substituent is preferably attached to an ortho-position with respect to the position of $Ar^2$ to which an oxygen atom is bonded. In the case where the unsaturated bond-containing substituent is attached to the ortho-position with respect to the position of $Ar^2$ to which the oxygen atom is bonded, the suppression of molecular motion due to steric hindrance can result in a lower dielectric loss tangent of a cured product to be obtained, which is preferred.

In an embodiment, the number of the unsaturated bond-containing substituents is preferably, but not particularly limited to, 1 to 6, preferably 2 to 6, more preferably 2 to 3. In a preferred embodiment, the number of the unsaturated bond-containing substituents is preferably the same as n described below from the viewpoint of easy introduction of the unsaturated bond-containing substituent.

In chemical formula (1) according to an embodiment, it is preferable that $Ar^1$ be a substituted or unsubstituted first aromatic hydrocarbon group having 6 to 30 carbon atoms and each $Ar^2$ be a substituted or unsubstituted second aromatic hydrocarbon group having 6 to 30 carbon atoms. It is more preferable that $Ar^1$ be represented by formula (2-1), (2-2), (2-6), (2-7), or (2-9) and each $Ar^2$ be represented by formula (3-1), (3-6), or (3-9). It is even more preferable that $Ar^1$ be represented by formula (2-1), (2-2), (2-6), or (2-7) and each $Ar^2$ be represented by formula (3-1) or (3-6). In the case where $Ar^1$ and each $Ar^2$ are the first aromatic hydrocarbon group and the second aromatic hydrocarbon group, respectively, an increase in dielectric constant due to lone-pair electrons can be prevented or inhibited, and a cured product to be obtained can have a lower dielectric loss tangent, which is preferred.

In chemical formula (1), n is an integer of 2 or 3. That is, the active ester compound has two or three ester bonds that link two aromatic rings. In an embodiment, from the viewpoint that a large number of ester bonds that can react with epoxy groups results in a higher cross-linking density to possibly increase the heat resistance, n is preferably 3. From the viewpoint that the active ester compound has low viscosity and thus good handleability, n is preferably 2.

Examples of a specific structure of the active ester compound represented by chemical formula (1) include, but are not particularly limited to, compounds represented by chemical formulae (4-1) to (4-43) below.

[Chem. 5]

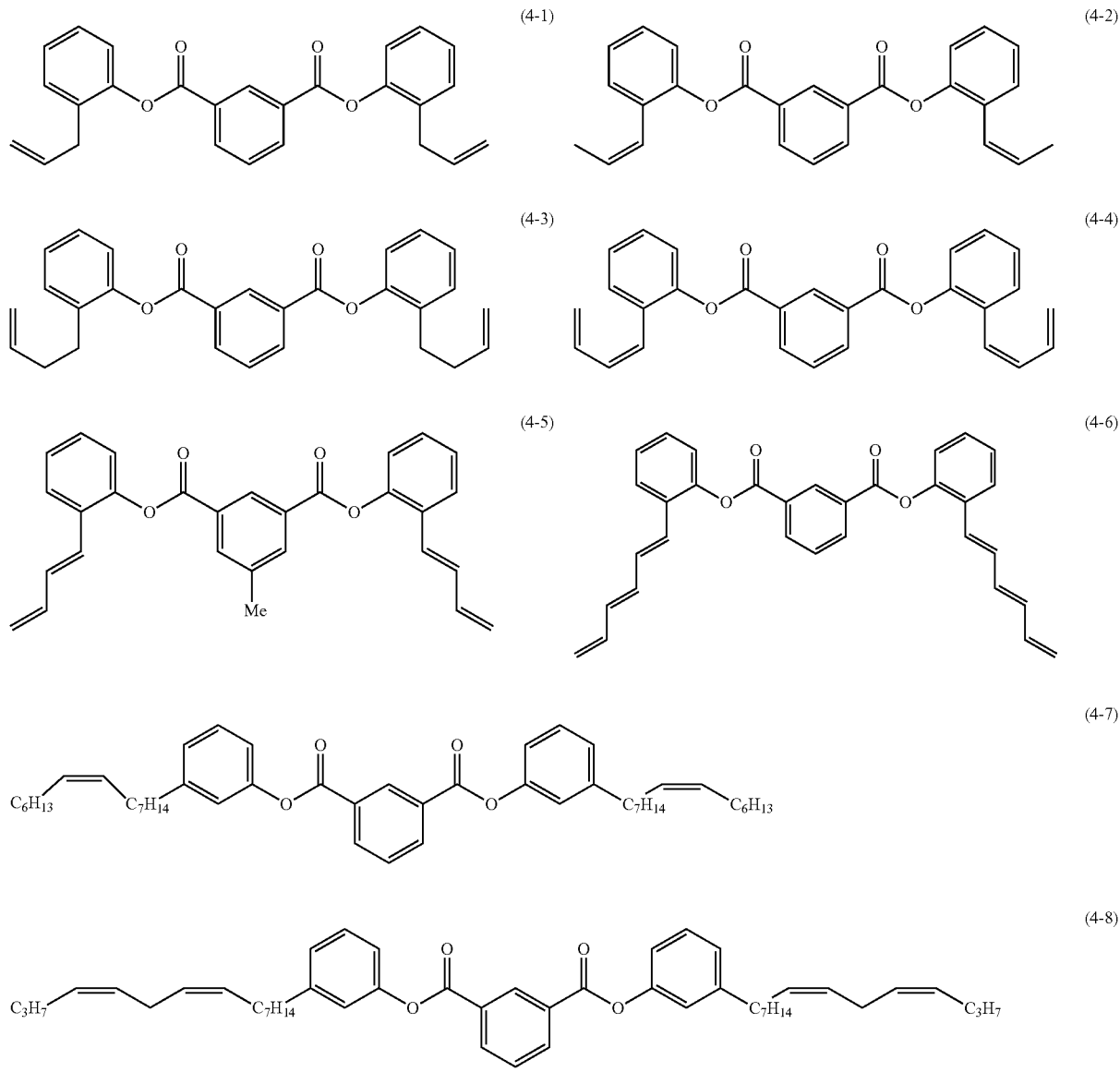

-continued
(4-9)
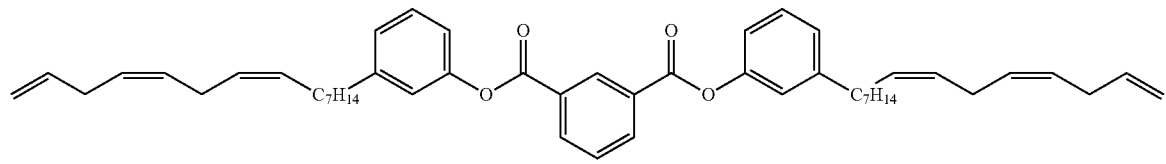
(4-10) (4-11)
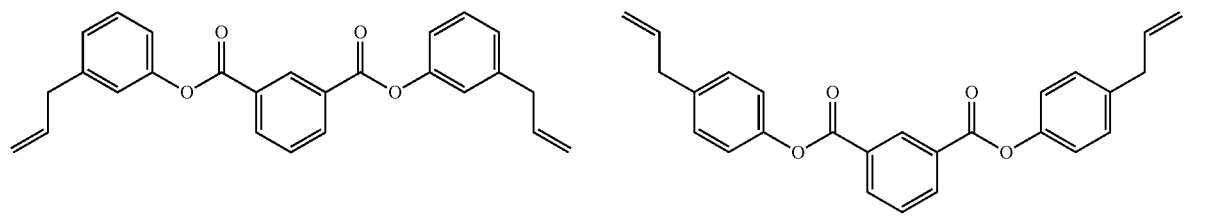
(4-12) (4-13)
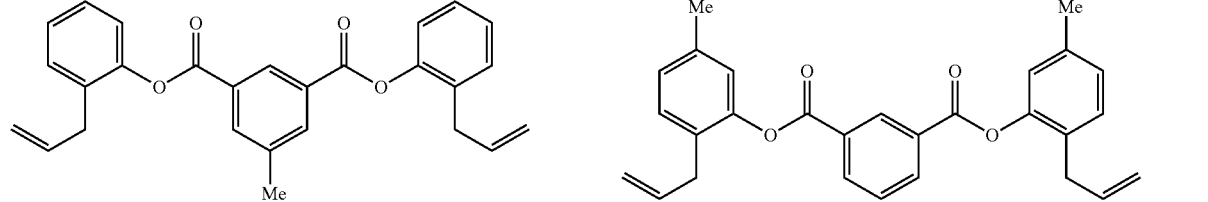
[Chem. 6]
(4-14) (4-15)
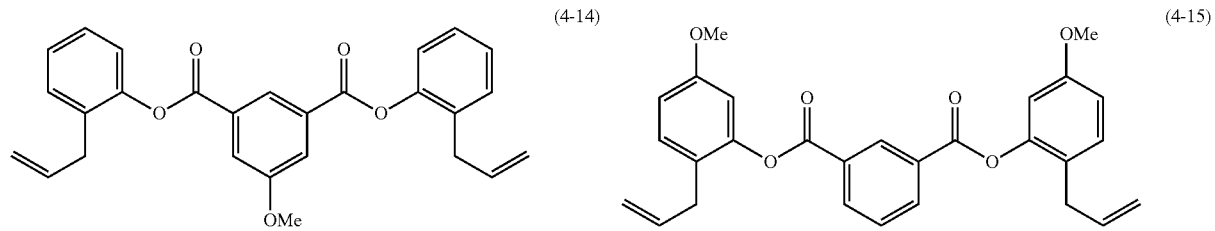
(4-16) (4-17)
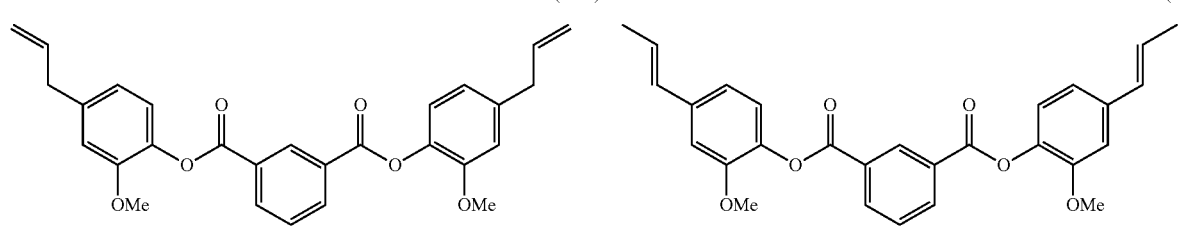
(4-18) (4-19)
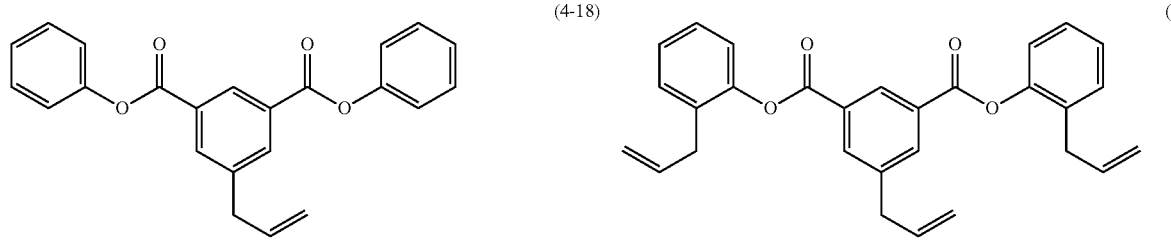
(4-20) (4-21)
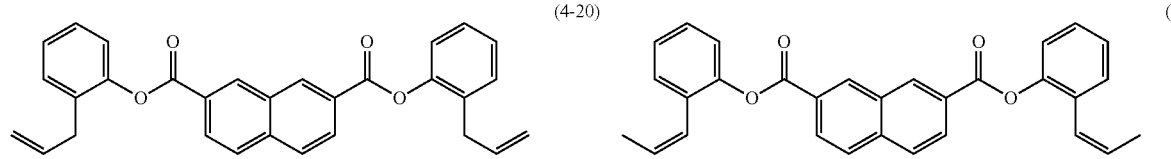

-continued
(4-22)
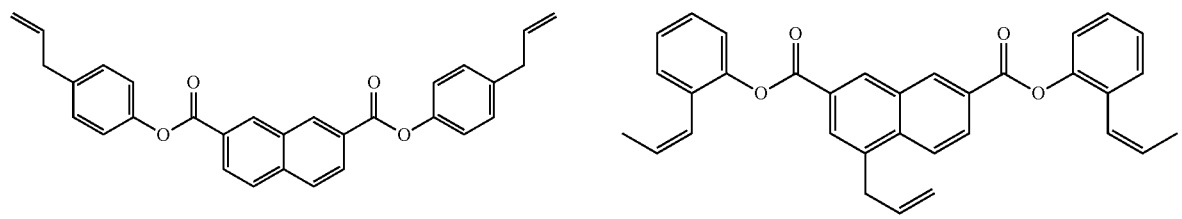
(4-23)
(4-24)
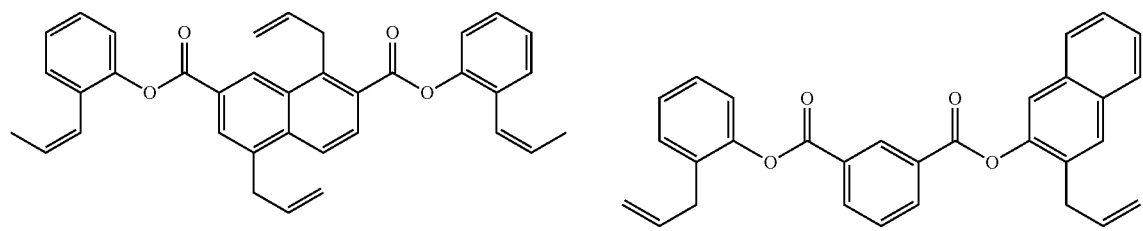
(4-25)
(4-26)
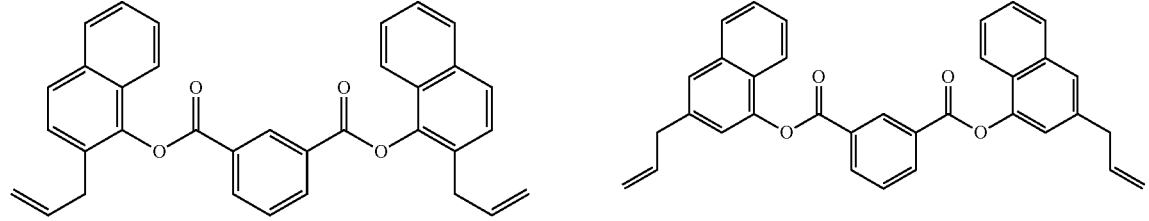
(4-27)
[Chem. 7]
(4-28)
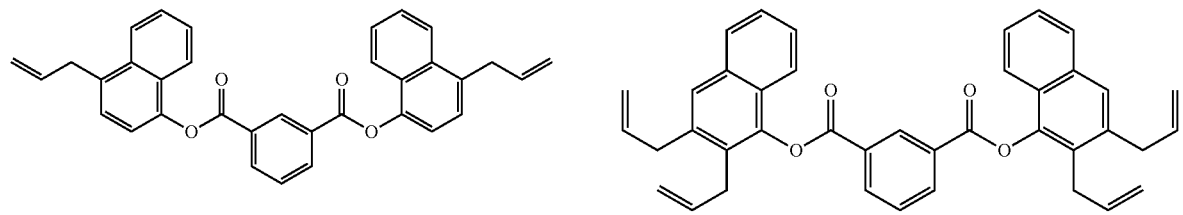
(4-29)
(4-30)
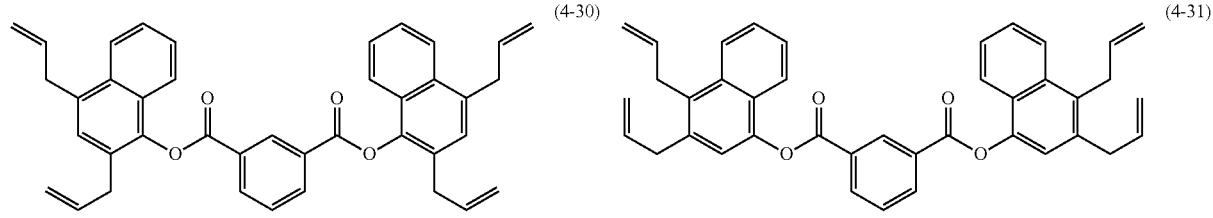
(4-31)
(4-32)
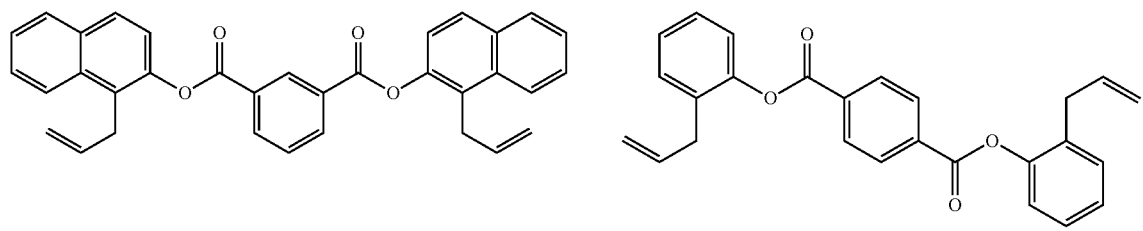
(4-33)

-continued
(4-34)
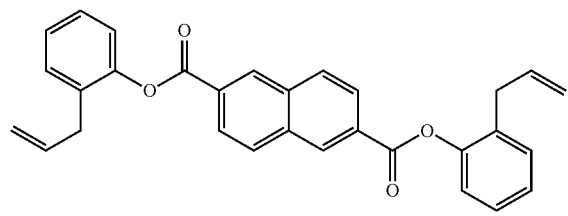
(4-35)
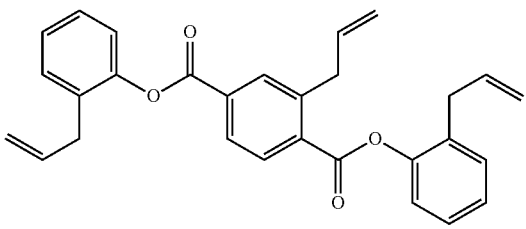
(4-36)
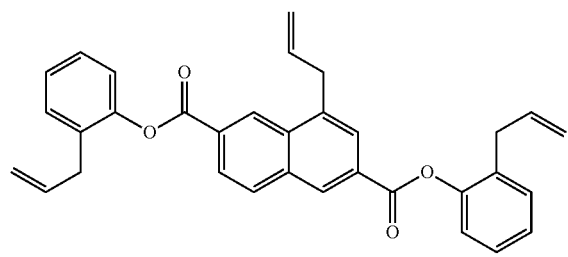
(4-37)
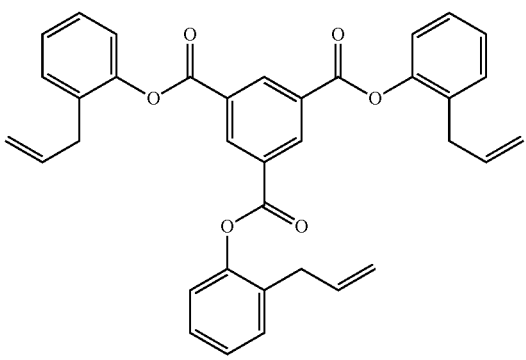
(4-38)
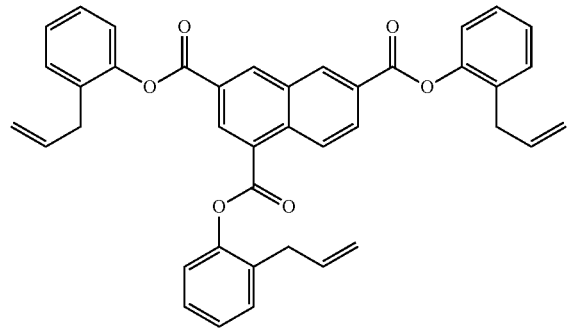
(4-39)
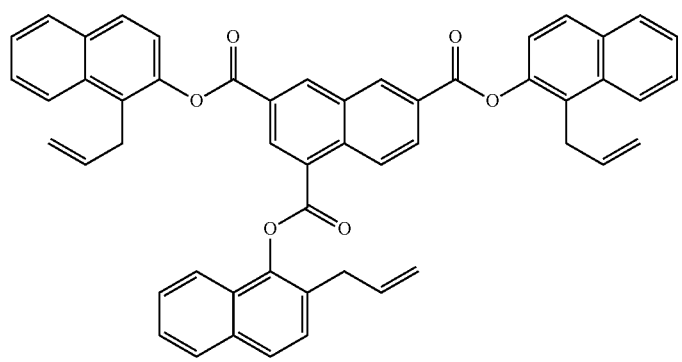
[Chem. 8]
(4-40)
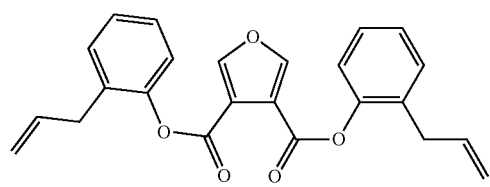
(4-41)
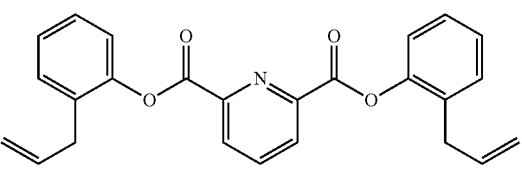

-continued (4-42)
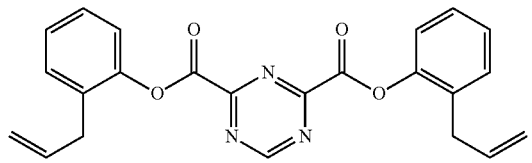

(4-43)
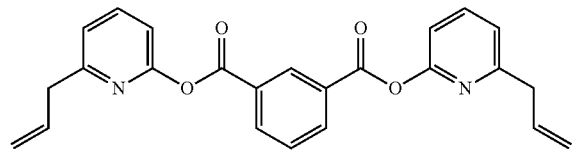

Among chemical formulae (4-1) to (4-43), chemical formulae (4-1) to (4-39) are preferred. Chemical formulae (4-1) to (4-3), (4-10) to (4-13), and (4-18) to (4-39) are more preferred. Chemical formulae (4-1) to (4-3), (4-12), (4-13), (4-19) to (4-21), (4-23) to (4-26), (4-29), (4-30), and (4-32) to (4-39) are even more preferred. Chemical formulae (4-1), (4-2), (4-12), (4-13), (4-26), (4-32), and (4-37) are particularly preferred.

From the viewpoint of achieving high handleability and low viscosity of the active ester compound, (4-1), (4-2), (4-12), and (4-13) are preferred. From the viewpoint of enabling the resulting cured product to have higher heat resistance and a good balance with low dielectric properties, (4-26), (4-32), and (4-37) are preferred.

<Method for Producing Active Ester Compound>

A method for producing the active ester compound is not particularly limited. The active ester compound can be produced by an appropriate known method.

The method according to an embodiment for producing the active ester compound includes a step of reacting a polycarboxylic acid compound containing the substituted or unsubstituted first aromatic ring group having 3 to 30 carbon atoms or its derivative with a phenol compound containing the substituted or unsubstituted second aromatic ring group having 3 to 30 carbon atoms.

In this case, it is preferred that at least one of the polycarboxylic acid compound or its derivative and the phenol compound have a substituted or unsubstituted unsaturated bond-containing substituent and the unsaturated bond-containing substituent have 2 to 30 carbon atoms.

(Polycarboxylic Acid Compound or its Derivative)

The polycarboxylic acid compound or its derivative has the substituted or unsubstituted first aromatic ring group. Examples of the "derivative of the polycarboxylic acid compound" include acid halides of carboxylic acids.

The first aromatic ring group and the substituent on the first aromatic ring group are the same as those described above.

Specific examples of the polycarboxylic acid compound or its derivative include compounds represented by chemical formulae (5-1) to (5-15) below.

[Chem. 9]

(5-1)
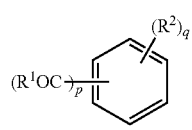

(5-2)
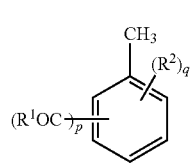

(5-3)
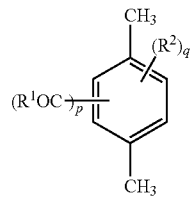

(5-4)
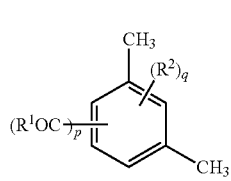

(5-5)
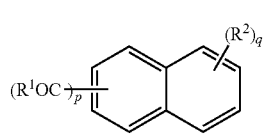

(5-6)
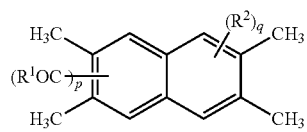

(5-7)
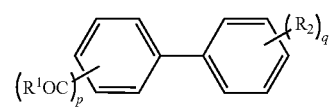

(5-8)
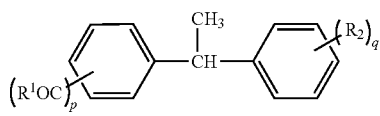

(5-9)
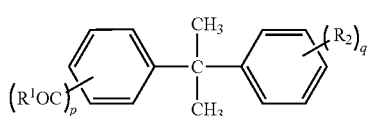

(5-10)
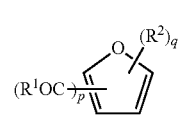

(5-11)
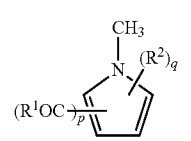

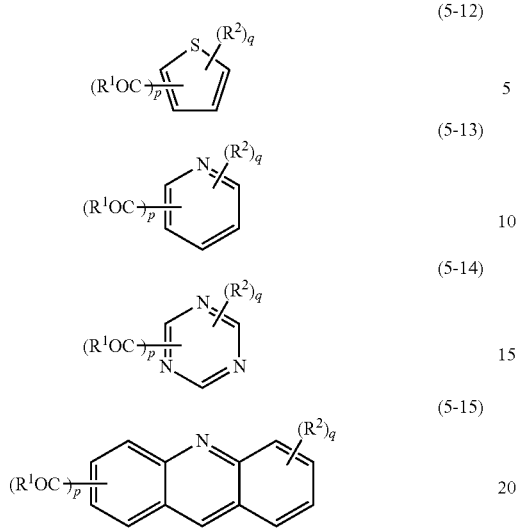

In chemical formulae (5-1) to (5-15), each $R^1$ is a hydroxy group or a halogen atom. Each $R^2$ is an unsaturated bond-containing substituent. In this case, the unsaturated bond-containing substituent is the same as that described above. Each p is 2 or 3. Each q is an integer of 0 to 1 or more, preferably 0 or 1 to 3, more preferably 0 or 1, even more preferably 0. In these chemical formulae, the substituents on the aromatic rings are illustrated on the same aromatic rings for convenience. However, for example, in chemical formula (5-7) or the like, the $R^1OC$ groups and the $R^2$ groups may be attached to different benzene rings, and the numbers of the substituents in one molecule are represented by p and q.

Specific examples of the polycarboxylic acid compound or its derivative include, but are not particularly limited to, benzenedicarboxylic acids, such as isophthalic acid, terephthalic acid, 5-allylisophthalic acid, and 2-allylterephthalic acid; benzenetricarboxylic acids, such as trimellitic acid and 5-allyltrimellitic acid; naphthalenedicarboxylic acids, such as naphthalene-1,5-dicarboxylic acid, naphthalene-2,3-dicarboxylic acid, naphthalene-2,6-dicarboxylic acid, naphthalene-2,7-dicarboxylic acid, 3-allylnaphthalene-1,4-dicarboxylic acid, and 3,7-diallylnaphthalene-1,4-dicarboxylic acid; pyridinetricarboxylic acids, such as 2,4,5-pyridinetricarboxylic acid; triazinecarboxylic acids, such as 1,3,5-triazine-2,4,6-tricarboxylic acid; and acid halides thereof. Among these, the third aromatic compound and so forth are preferably benzenedicarboxylic acid or benzenetricarboxylic acid, more preferably isophthalic acid, terephthalic acid, isophthaloyl chloride, terephthaloyl chloride, 1,3,5-benzenetricarboxylic acid, or 1,3,5-benzenetricarbonyl trichloride, even more preferably isophthaloyl chloride, terephthaloyl chloride, or 1,3,5-benzenetricarbonyl trichloride.

These polycarboxylic acid compounds or their derivatives may be used alone or in combination of two or more.

(Phenol Compound)

The phenol compound has a substituted or unsubstituted aromatic ring group and preferably has 3 to 30 carbon atoms. In this case, the aromatic ring group and the substituent of the aromatic ring group are the same as those described above.

Specific examples of the phenol compound include compounds represented by chemical formulae (6-1) to (6-17) below.

[Chem. 10]

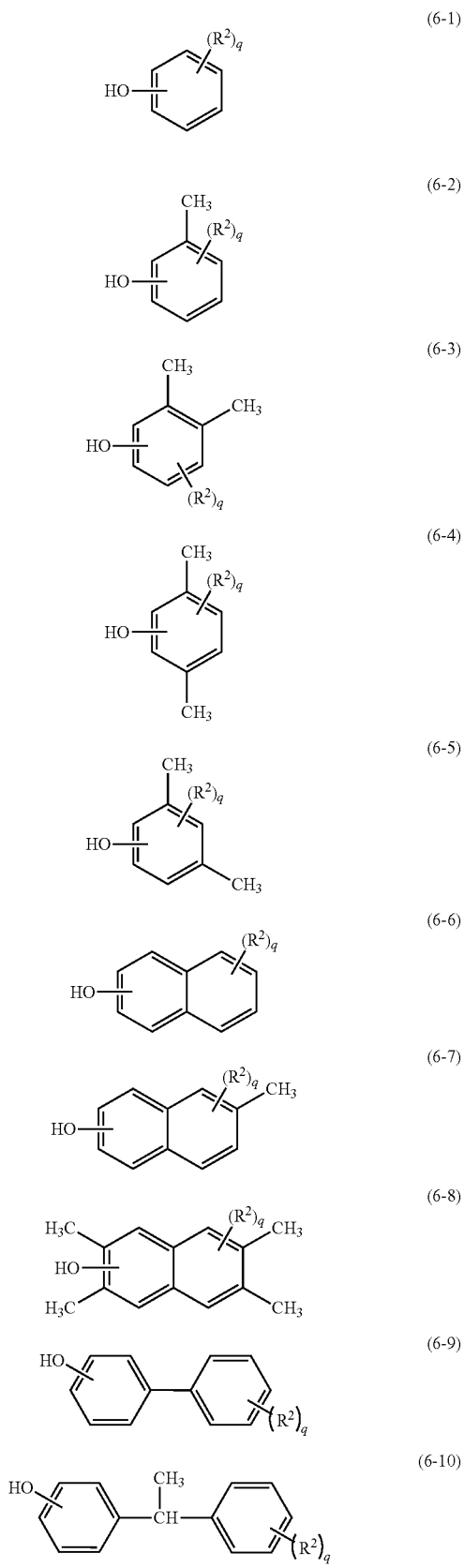

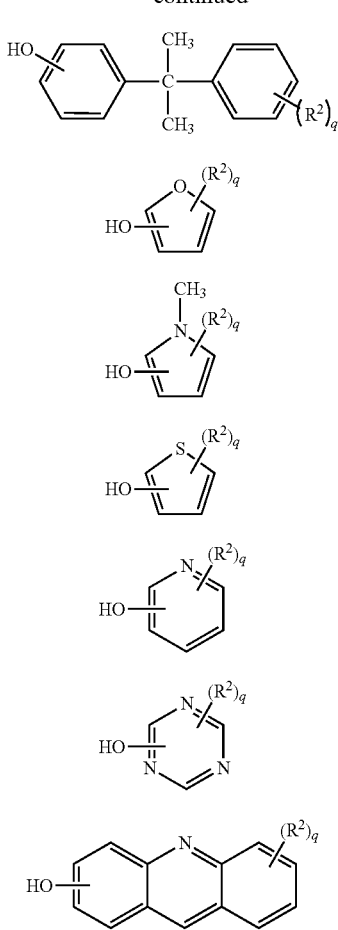

In chemical formulae (6-1) to (6-17), each $R^2$ is an unsaturated bond-containing substituent. In this case, the unsaturated bond-containing substituent is the same as described above. Each q is an integer of 0 or 1 or more, preferably 1 to 3, more preferably 1 or 2, even more preferably 1. In the case where q is 2 or more, binding positions on an aromatic ring are freely selected. For example, in the cases of the naphthalene ring in chemical formula (6-6) and the heterocyclic ring in chemical formula (6-17), any ring may be substituted. In the case of chemical formula (6-9) or the like, any of the benzene rings present in one molecule may be substituted. The number of substituents in one molecule is q.

Specific examples of the phenol compound include, but are not particularly limited to, phenol; naphthol; allyl phenols, such as 2-allylphenol, 3-allylphenol, 4-allylphenol, 4-methyl-2-allylphenol, 6-methyl-2-allylphenol, and eugenol; propenyl alcohols, such as 2-(1-propenyl)phenol and isoeugenol; butenylphenols, such as 2-(3-butenyl)phenol and 2-(1-ethyl-3-butenyl)phenol; long-chain alkenylphenols, such as cardanol; and allylnaphthols, such as 2-allyl-1-naphthol, 1-allyl-2-naphthol, 3-allyl-1-naphthol, and 3-allyl-1-naphthol. Among these, the phenol compound is preferably allylphenol or allylnaphthol, more preferably 2-allylphenol, 4-methyl-2-allylphenol, 6-methyl-2-allylphenol, 2-allyl-1-naphthol, or 1-allyl-2-naphthol, even more preferably 2-allylphenol, 2-allyl-1-naphthol, or 1-allyl-2-naphthol.

From the viewpoint of achieving high handleability and low viscosity of an esterified compound, for example, 2-allylphenol having a benzene ring skeleton is preferred. From the viewpoint of enabling the resulting cured product to have higher heat resistance and a good balance with low dielectric properties, for example, 2-allyl-1-naphthol or 1-allyl-2-naphthol having a naphthalene ring skeleton is preferred.

These phenol compounds described above or their derivatives may be used alone or in combination of two or more.

The amounts of the polycarboxylic acid compound or its derivative and the phenol compound are not particularly limited. The molar ratio of the number of moles of carboxy groups and/or derivative groups, such as acyl halide groups, to the number of moles of hydroxy groups of the phenol compound [(carboxy groups and/or derivative groups, such as acyl halide groups)/(hydroxy groups)] is preferably 0.8 to 3.0, more preferably 0.9 to 2.0, even more preferably 1.0 to 1.2.

Reaction conditions are not particularly limited, and a known method can be employed as appropriate.

The pH during the reaction is preferably, but not particularly limited to, 11 or more. In this case, the pH can be adjusted with an acid, such as hydrochloric acid, sulfuric acid, nitric acid, or acetic acid, or a base, such as sodium hydroxide, potassium hydroxide, calcium hydroxide, or ammonia.

The reaction temperature is preferably, but not particularly limited to, 20° C. to 100° C., more preferably 40° C. to 80° C.

The reaction pressure is more preferably, but not particularly limited to, normal pressure.

The reaction time is preferably, but not particularly limited to, 0.5 to 10 hours, more preferably 1 to 5 hours.

<Composition>

According to an embodiment of the present invention, a composition is provided. The composition contains an active ester compound and an epoxy resin. The composition may further contain another resin, a solvent, another curing agent, an additive, and so forth, as needed.

[Active Ester Compound]

As the active ester compound, the active ester compound according to the present invention is contained. The active ester compound has, for example, the function of a curing agent for the epoxy resin.

The active ester compound described above is used; thus, the description thereof is omitted here.

The active ester compound content is preferably, but not particularly limited to, 2% to 80% by mass, more preferably 5% to 70% by mass based on the solid content of the composition. An active ester compound content of 2% or more by mass results in a lower dielectric loss tangent of a cured product thereof and is thus preferred. An active ester compound content of 80% or less by mass results in a good balance between the heat resistance and the dielectric loss tangent of a cured product thereof and is thus preferred. In the present specification, the "solid content of the composition" refers to the total mass of components in the composition excluding the solvent.

In an embodiment, the mass ratio of the amount of the active ester compound used to the amount of the epoxy resin used (active ester compound/epoxy resin) is preferably more than 1.0, more preferably 1.1 to 5.0, even more preferably 1.2 to 3.0. A mass ratio of more than 1.0 results in a lower dielectric loss tangent of a cured product thereof and is thus preferred. Typically, when the amount of the active ester compound used is larger than the amount of the epoxy resin used, the dielectric loss tangent decreases as the amount of the active ester compound used increases relatively. However, the presence of the active ester compound unreacted with the epoxy resin tends to reduce the heat resistance. In contrast, even if the active ester compound according to the embodiment does not react with the epoxy resin, the unsaturated bond-containing substituents themselves form cross-links; thus, the heat resistance of a cured product can be maintained. In other words, the low dielectric loss tangent can be achieved while maintaining the heat resistance of the cured product.

Examples of the third aromatic compound or its derivative include, but are not particularly limited to, among the polycarboxylic acid compounds and their derivatives described above, those having no unsaturated bond-containing substituent.

In an embodiment, examples of another active ester compound include compounds represented by chemical formula (7) below.

[Chem. 11]

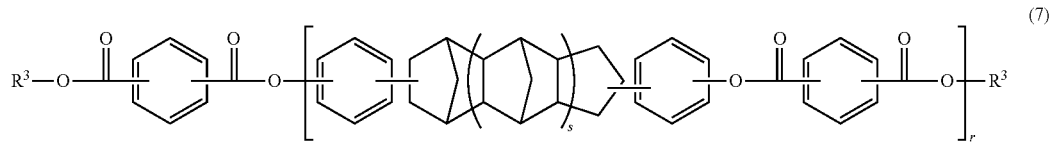

(7)

[Another Curing Agent]

In an embodiment, another curing agent may be used together with the active ester compound according to the present invention.

Examples of another curing agent include, but are not particularly limited to, another active ester compound, amine curing agents, imidazole curing agents, acid anhydride curing agents, and phenolic resin curing agents.

An example of another active ester compound described above is, but not particularly limited to, an active ester compound other than the foregoing active ester compounds (in this specification, referred to as "another active ester compound"). Specific examples of another active ester compound include, but are not particularly limited to, reaction products of a first aromatic compound having two or more phenolic hydroxy groups, a second aromatic compound having a phenolic hydroxy group, and a third aromatic compound having two or more carboxy groups or its derivative. In this case, another active ester compound has not unsaturated bond-containing substituent in its molecule.

Examples of the first aromatic compound include, but are not particularly limited to, polyhydric phenol compounds and polymers of phenolic hydroxy group-containing compounds and polymerizable compounds.

Examples of the polyhydric phenol compounds include catechol, resorcinol, hydroquinone, bisphenol A, bisphenol F, 1,5-dihydroxynaphthalene, 1,6-dihydroxynaphthalene, 2,6-dihydroxynaphthalene, dihydroxybenzophenone, trihydroxybenzophenone, and tetrahydroxybenzophenone.

Examples of the phenolic hydroxy group-containing compounds include, but are not particularly limited to, the polyhydric phenol compounds, phenol, 1-naphthol, 2-naphthol, o-cresol, m-cresol, and p-cresol.

Examples of the polymerizable compounds include, but are not particularly limited to, aliphatic diene compounds, such as 1,3-butadiene, 1,5-hexadiene, dicyclopentadiene, tricyclopentadiene, tetracyclopentadiene, pentacyclopentadiene, and hexacyclopentadiene; aromatic diene compounds, such as divinylbenzene and divinylbiphenyl; and alkoxymethyl compounds, such as dimethoxymethylbenzene, dimethoxymethylbiphenyl, methoxy adducts of bisphenol A, ethoxy adducts of bisphenol A, methoxy adducts of bisphenol F, and ethoxy adducts of bisphenol F.

Examples of the second aromatic compound include, but are not particularly limited to, phenol compounds that have no unsaturated bond-containing substituent among the foregoing phenol compounds.

In chemical formula (7), each $R^3$ is independently phenyl or naphthyl. Each s is independently 0 or 1. r is an average of 0.05 to 2.5.

Examples of the amine curing agents include, but are not particularly limited to, aliphatic amines, such as diethylenetriamine (DTA), triethylenetetramine (TTA), tetraethylenepentamine (TEPA), dipropylenediamine (DPDA), diethylaminopropylamine (DEAPA), N-aminoethylpiperazine, menthanediamine (MDA), isophoronediamine (IPDA), 1,3-bisaminomethylcyclohexane (1,3-BAC), piperidine, N,N,-dimethylpiperazine, and triethylenediamine; and aromatic amines, such as m-xylenediamine (XDA), methanephenylenediamine (MPDA), diaminodiphenylmethane (DDM), diaminodiphenyl sulfone (DDS), benzylmethylamine, 2-(dimethylaminomethyl)phenol, and 2,4,6-tris(dimethylaminomethyl)phenol.

Examples of the imidazole curing agents include 2-methylimidazole, 2-ethyl-4-methylimidazole, 1-cyanoethyl-2-undecylimidazolium trimellitate, and epoxy-imidazole adducts.

Examples of the acid anhydride curing agents include phthalic anhydride, trimellitic anhydride, pyromellitic anhydride, benzophenonetetracarboxylic dianhydride, ethylene glycol bistrimellitate, glycerol tristrimellitate, maleic anhydride, tetrahydrophthalic anhydride, methyltetrahydrophthalic anhydride, endo-methylenetetrahydrophthalic anhydride, methyl-endo-methylenetetrahydrophthalic anhydride, methylbutenyltetrahydrophthalic anhydride, dodecenylsuccinic anhydride, hexahydrophthalic anhydride, methylhexahydrophthalic anhydride, succinic anhydride, and methylcyclohexenedicarboxylic anhydride.

Examples of the phenolic resin curing agents include phenolic novolac resins, cresol novolac resins, naphthol novolac resins, bisphenol novolac resins, biphenyl novolac resins, dicyclopentadiene phenol addition-type resins, phenol aralkyl resins, naphthol aralkyl resins, triphenolmethane-type resins, tetraphenolethane-type resins, and aminotriazine-modified phenolic resins.

These curing agents described above may be used alone or in combination of two or more.

The amount of another curing agent contained is preferably, but not particularly limited to, 2% to 80% by mass, more preferably 5% to 70% by mass with respect to the active ester compound. When the amount of the curing agent contained is 2% or more by mass, fast curability is also provided, which is preferred. When the amount of the curing agent contained is 80% or less by mass, a cured product also has good mechanical properties, which is preferred.

[Epoxy Resin]

The epoxy resin is a curable resin that contains two or more epoxy groups in its molecule and that can be cured by forming a cross-linked network with the epoxy groups.

Examples of the epoxy resin include, but are not particularly limited to, phenol novolac-type epoxy resins, such as epoxy resins, cresol novolac-type epoxy resins, α-naphthol novolac-type epoxy resins, β-naphthol novolac-type epoxy resins, bisphenol A novolac-type epoxy resins, and biphenyl novolac-type epoxy resins; aralkyl-type epoxy resins, such as phenol aralkyl-type epoxy resins, naphthol aralkyl-type epoxy resins, and phenol biphenylaralkyl-type epoxy resins; bisphenol-type epoxy resins, such as bisphenol A-type epoxy resins, bisphenol AP-type epoxy resins, bisphenol AF-type epoxy resins, bisphenol B-type epoxy resins, bisphenol BP-type epoxy resins, bisphenol C-type epoxy resins, bisphenol E-type epoxy resins, bisphenol F-type epoxy resins, bisphenol S-type epoxy resins, and tetrabromobisphenol A-type epoxy resins; biphenyl-type epoxy resins, such as biphenyl-type epoxy resins, tetramethylbiphenyl-type epoxy resins, and epoxy resins having biphenyl skeletons and diglycidyloxybenzene skeletons; naphthalene-type epoxy resins; binaphthol-type epoxy resins; binaphthyl-type epoxy resins; dicyclopentadiene-type epoxy resins, such as dicyclopentadiene phenol-type epoxy resins; glycidylamine-type epoxy resins, such as tetraglycidyldiaminodiphenylmethane-type epoxy resins, triglycidyl-p-aminophenol-type epoxy resins, and diaminodiphenyl sulfone glycidylamine-type epoxy resins; diglycidyl ester-type epoxy resins, such as diglycidyl 2,6-naphthalenedicarboxylate-type epoxy resins and hexahydrophthalic anhydride glycidyl ester-type epoxy resins; and benzopyran-type epoxy resins, such as dibenzopyran, hexamethyldibenzopyran, and 7-phenylhexamethyldibenzopyran.

Among these, phenol biphenylaralkyl-type epoxy resins, naphthol aralkyl-type epoxy resins, and dicyclopentadiene phenol-type epoxy resins are preferred.

These epoxy resins may be used alone or in combination of two or more.

The epoxy resin preferably has an epoxy equivalent of 150 to 500 g/equivalent (eq.), more preferably 200 to 350 g/equivalent. An epoxy equivalent of the epoxy resin of 150 g/equivalent or more results in higher heat resistance of a cured product to be obtained and is thus preferred. An epoxy equivalent of the epoxy resin of 500 g/equivalent or less results in a better balance between the heat resistance and the dielectric loss tangent of a cured product to be obtained and is thus preferred.

The epoxy resin preferably has a weight-average molecular weight of 200 to 5,000, more preferably 300 to 3,000. A weight-average molecular weight of the epoxy resin of 200 or more also results in fast curability and is thus preferred. A weight-average molecular weight of the epoxy resin of 5,000 or less results in good formability and is thus preferred. As the value of the "weight-average molecular weight" in the present specification, a value measured by a method described below is used. Specifically, a value obtained by gel permeation chromatography (GPC) measurement under conditions below is used.

Measurement Conditions of GPC

Measurement instrument: "HLC-8320 GPC", available from Tosoh Corporation

Column: guard column "HXL-L", available from Tosoh Corporation

"TSK-GEL G4000HXL", available from Tosoh Corporation

"TSK-GEL G3000HXL", available from Tosoh Corporation

"TSK-GEL G2000HXL", available from Tosoh Corporation

"TSK-GEL G2000HXL", available from Tosoh Corporation

Detector: RI (differential refractometer)

Data processing: "GPC Workstation EcoSEC-WorkStation", available from Tosoh Corporation Column temperature: 40° C.

Developing solvent: tetrahydrofuran

Flow rate: 1.0 ml/minute

Standard: monodisperse polystyrenes having known molecular weights, described below, were used in accordance with the measurement manual of "GPC-8320 GPC".

Polystyrene Used:

"A-500", available from Tosoh Corporation
"A-1,000", available from Tosoh Corporation
"A-2,500", available from Tosoh Corporation
"A-5,000", available from Tosoh Corporation
"F-1", available from Tosoh Corporation
"F-2", available from Tosoh Corporation
"F-4", available from Tosoh Corporation
"F-10", available from Tosoh Corporation
"F-20", available from Tosoh Corporation
"F-40", available from Tosoh Corporation
"F-80", available from Tosoh Corporation
"F-128", available from Tosoh Corporation Sample: a filtrate (50 µl) obtained by filtering a 1.0% by mass solution in tetrahydrofuran with a microfilter in terms of the resin solid content The epoxy resin content is preferably, but not particularly limited to, 2% to 80% by mass, more preferably 5% to 70% by mass with respect to the active ester compound. An epoxy resin content of 2% or more by mass results in good formability and is thus preferred. An epoxy resin content of 80% or less by mass results in a better balance between the dielectric properties and the heat resistance of a cured product and is thus preferred.

[Another Resin]

In an embodiment, the composition may contain another resin. In this specification, the term "another resin" refers to a resin other than the epoxy resin.

Specific examples of another resin include, but are not particularly limited to, maleimide resins, bismaleimide resins, polymaleimide resins, poly(phenylene ether) resins, polyimide resins, cyanate ester resins, benzoxazine resins, triazine-containing cresol novolac resins, cyanic ester resins, cyanic ester resins, styrene-maleic anhydride resins, ally group-containing resins, such as diallyl bisphenol and triallyl isocyanurate, polyphosphate esters, and phosphoric ester-carbonate copolymers. These resins may be used alone or in combination of two or more.

[Solvent]

In an embodiment, the composition may contain a solvent. The solvent has, for example, the function of adjusting the viscosity of the composition.

Specific examples of the solvent include, but are not particularly limited to, ketones, such as acetone, methyl ethyl ketone, and cyclohexanone; esters, such as ethyl acetate, butyl acetate, cellosolve acetate, propylene glycol monomethyl ether acetate, and carbitol acetate; carbitols, such as cellosolve and butyl carbitol; aromatic hydrocarbons, such as toluene and xylene; and amides, such as dimethylformamide, dimethylacetamide, and N-methylpyrrolidone. These solvents may be used alone or in combination of two or more.

The amount of the solvent used is preferably 10% to 80% by mass, more preferably 20% to 70% by mass based on the total mass of the composition. When the amount of the solvent used is 10% or more by mass, good handleability is provided, which is preferred. When the amount of the solvent used is 80% or less by mass, good impregnation properties with another base material are provided, which is preferred.

[Additive]

In an embodiment, the composition may contain an additive. Examples of the additive include curing accelerators, flame retardants, and fillers.

(Curing Accelerator)

Examples of the curing accelerators include, but are not particularly limited to, phosphorus-based curing accelerators, amine-based curing accelerators, imidazole-based curing accelerators, guanidine-based curing accelerators, urea-based curing accelerators, peroxides, and azo compounds.

Examples of the phosphine-based curing accelerators include, organic phosphine compounds, such as triphenylphosphine, tributylphosphine, tri(p-tolyl)phosphine, diphenylcyclohexylphosphine, and tricyclohexylphosphine; organic phosphite compounds, such as trimethyl phosphite and triethyl phosphite; and phosphonium salts, such as ethyltriphenylphosphonium bromide, benzyltriphenylphosphonium chloride, butylphosphonium tetraphenylborate, tetraphenylphosphonium tetraphenylborate, tetraphenylphosphonium tetra-p-tolylborate, triphenylphosphine-triphenylborane, tetraphenylphosphonium thiocyanate, tetraphenylphosphonium dicyanamide, butylphenylphosphonium dicyanamide, and tetrabutylphosphonium decanoate.

Examples of the amine-based curing accelerators include triethylamine, tributylamine, N,N-dimethyl-4-aminopyridine (DMAP), 2,4,6-tris(dimethylaminomethyl)phenol, 1,8-diazabicyclo[5,4,0]-undecene-7 (DBU), and 1,5-diazabicyclo[4,3,0]-nonene-5 (DBN).

Examples of the imidazole-based curing accelerators include 2-methylimidazole, 2-undecylimidazole, 2-heptadecylimidazole, 1,2-dimethylimidazole, 2-ethyl-4-methylimidazole, 2-phenylimidazole, 2-phenyl-4-methylimidazole, 1-benzyl-2-methylimidazole, 1-benzyl-2-phenylimidazole, 1-cyanoethyl-2-methylimidazole, 1-cyanoethyl-2-undecylimidazole, 1-cyanoethyl-2-ethyl-4-methylimidazole, 1-cyanoethyl-2-phenylimidazole, 1-cyanoethyl-2-undecylimidazolium trimellitate, 1-cyanoethyl-2-phenylimidazolium trimellitate, an isocyanuric acid adduct of 2-phenylimidazole, 2-phenyl-4,5-dihydroxymethylimidazole, 2-phenyl-4-methyl-5hydroxymethylimidazole, 2,3-dihydro-IH-pyrrolo[1,2-a]benzimidazole, 1-dodecyl-2-methyl-3-benzylimidazolium chloride, and 2-methylimidazoline.

Examples of the guanidine-based curing accelerators include dicyandiamide, 1-methylguanidine, 1-ethylguanidine, 1-cyclohexylguanidine, 1-phenylguanidine, dimethylguanidine, diphenylguanidine, trimethylguanidine, tetramethylguanidine, pentamethylguanidine, 1,5,7-triazabicyclo[4.4.0]dec-5-ene, 7-methyl-1,5,7-triazabicyclo[4.4.0]dec-5-ene, 1-methylbiguanide, 1-ethylbiguanide, 1-butylbiguanide, 1-cyclohexylbiguanide, 1-allybiguanide, and 1-phenylbiguanide.

Examples of the urea-based curing accelerators include 3-phenyl-1,1-dimethylurea, 3-(4-methylphenyl)-1,1-dimethylurea, chlorophenylurea, 3-(4-chlorophenyl)-1,1-dimethylurea, and 3-(3,4-dichlorophenyl)-1,1-dimethylurea.

Examples of the peroxides and the azo compounds include benzoyl peroxide, p-chlorobenzoyl peroxide, di-tert-butyl peroxide, diisopropyl peroxycarbonate, di-2-ethylhexyl peroxycarbonate, and azobisisobutyronitrile.

Among these curing accelerators, 2-ethyl-4-methylimidazole or dimethylaminopyridine is preferably used.

These curing accelerators described above may be used alone or in combination of two or more.

The amount of the curing accelerator used is preferably 0.01 to 5 parts by mass, more preferably 0.1 to 3 based on 100 parts by mass of the epoxy resin. When the amount of the curing accelerator used is 0.01 parts or more by mass, good curability is obtained, which is preferred. When the amount of the curing accelerator used is 5 parts or less by mass, good formability is obtained, which is preferred.

(Flame Retardant)

Examples of the flame retardants include, but are not particularly limited to, inorganic phosphorus-based flame retardants, organic phosphorus-based flame retardants, and halogen-containing flame retardants.

Examples of the inorganic phosphorus-based flame retardants include, but are not particularly limited to, red phosphorus; ammonium phosphates, such as ammonium phosphate monobasic, ammonium phosphate dibasic, ammonium phosphate tribasic, and ammonium polyphosphate; and phosphoramide.

Examples of the organic phosphorus-based flame retardants include, but are not particularly limited to, phosphoric esters, such as methyl acid phosphate, ethyl acid phosphate, isopropyl acid phosphate, dibutyl phosphate, monobutyl phosphate, butoxyethyl acid phosphate, 2-ethylhexyl acid phosphate, bis(2-ethylhexyl)phosphate, monoisodecyl acid phosphate, lauryl acid phosphate, tridecyl acid phosphate, stearyl acid phosphate, isostearyl acid phosphate, oleyl acid phosphate, butyl pyrophosphate, tetracosyl acid phosphate, ethylene glycol acid phosphate, and (2-hydroxyethyl) methacrylate acid phosphate; diphenylphosphines, such as 9,10-dihydro-9-oxa-10-phosphaphenanthrene-10-oxide and diphenylphosphine oxide; phosphorus-containing phenols, such as 10-(2,5-dihydroxyphenyl)-10H-9-oxa-10-phosphaphenanthrene-10-oxide, 10-(1,4-dioxynaphthalene)-10H-9-oxa-10-phosphaphenanthrene-10-oxide, diphenylphosphinyl hydroquinone, diphenylphosphenyl-1,4-dioxynaphthalene, 1,4-cyclooctylenephosphinyl-1,4-phenyldiol, and 1,5-cyclooctylenephosphinyl-1,4-phenyldiol; cyclic phosphorus compounds, such as 9,10-dihydro-9-oxa-10-phosphaphenanthrene-10-oxide, 10-(2,5-dihydrooxyphenyl)-10H-9-oxa-10-phosphaphenanthrene-10-oxide, and 10-(2,7-dihydrooxynaphthyl)-10H-9-oxa-10-phosphaphenanthrene-10-oxide; and compounds obtained by reacting the phosphoric esters, the diphenylphosphines, or the phosphorus-containing phenols with epoxy resins, aldehyde compounds, or phenol compounds.

Examples of the halogen-containing flame retardants include, but are not particularly limited to, brominated polystyrene, bis(pentabromophenyl)ethane, tetrabromobisphenol A bis(dibromopropyl ether), 1,2-bis(tetrabromophthalimide), 2,4,6-tris(2,4,6-tribromophenoxy)-1,3,5-triazine, and tetrabromophthalic acid.

These flame retardants described above may be used alone or in combination of two or more.

The amount of the flame retardant used is preferably 0.1 to 50 parts by mass, more preferably 1 to 30 based on 100 parts by mass of the epoxy resin. When the amount of the flame retardant used is 0.1 parts or more by mass, flame retardancy can be imparted, which is preferred. When the amount of the flame retardant used is 50 parts or less by mass, flame retardancy can be imparted while maintaining the dielectric properties, which is preferred.

(Filler)

Examples of the fillers include organic fillers and inorganic fillers. The fillers have, for example, the functions of improving elongation and mechanical strength.

Examples of the organic fillers include, but are not particularly limited to, polyamide particles.

Examples of the inorganic fillers include, but are not particularly limited to, silica, alumina, glass, cordierite, silicon oxide, barium sulfate, barium carbonate, aluminum hydroxide, magnesium hydroxide, calcium carbonate, magnesium carbonate, magnesium oxide, boron nitride, aluminum nitride, manganese nitride, aluminum borate, strontium carbonate, strontium titanate, calcium titanate, magnesium titanate, bismuth titanate, titanium oxide, zirconium oxide, barium titanate, barium zirconate titanate, barium zirconate, calcium zirconate, zirconium phosphate, zirconium phosphate tungstate, talc, clay, mica powder, zinc oxide, hydrotalcite, boehmite, and carbon black.

Among these, silica is preferably used. In this case, Examples of silica that can be used include amorphous silica, fused silica, crystalline silica, synthetic silica, and hollow silica.

The fillers described above may be surface-treated as needed. Examples of a surface treatment agent that can be used in this case include, but are not particularly limited to, aminosilane-based coupling agents, epoxysilane-based coupling agents, mercaptosilane-based coupling agents, silane-based coupling agents, organosilazane compounds, and titanate-based coupling agents. Specific examples of the surface treatment agents include 3-glycidoxypropyltrimethoxysilane, 3-mercaptopropyltrimethoxysilane, 3-aminopropyltriethoxysilane, N-phenyl-3-aminopropyltrimethoxysilane, and hexamethyldisilazane.

These fillers described above may be used alone or in combination of two or more.

The average particle size of each of the fillers is preferably, but is not particularly limited to, 0.01 to 10 μm, more preferably 0.03 to 5 μm, even more preferably 0.05 to 3 μm. In the present specification, the "particle size" refers to the maximum distance between two points on the outline of a particle. The "average particle size" refers to a value obtained by a method including measuring the particle sizes of freely-selected 100 particles on one screen in an image with a scanning electron microscope (SEM) and calculating the average value thereof.

The amount of the filler used is preferably 0.5 to 95 parts by mass, more preferably 5 to 80 parts by mass based on 100 parts by mass of the epoxy resin. When the amount of the filler used is 0.5 parts or more by mass, low thermal expansion can be provided, which is preferred. When the amount of the filler used is 95 parts or less by mass, a good balance between characteristics and formability is provided, which is preferred.

<Cured Product (Cured Product of Active Ester Compound)>

According to an embodiment of the present invention, a cured product obtained by curing the active ester compound is provided.

Because the active ester compound described above has an unsaturated bond-containing substituent, it can be homopolymerized to provide a cured product.

The cured product may contain the curing agent, the additive, the curing accelerator, and so forth as needed.

Because the active ester compound itself has a low dielectric loss tangent, a cured product of the resulting homopolymer can also have a low dielectric loss tangent. Thus, the cured product can be suitably used for applications of printed circuit boards and build-up films.

The heating temperature for heat curing is preferably, but not particularly limited to, 150° C. to 300° C., more preferably 175° C. to 250° C.

<Cured Product (Cured Product of Composition)>

According to an embodiment of the present invention, a cured product obtained by curing the composition described above is provided. The cured product has a low dielectric loss tangent and higher heat resistance and thus can be used for electronic material applications of, for example, semiconductor package substrates, printed circuit boards, build-up adhesive films, and semiconductor sealing materials. Additionally, the cured product can also be used for applications of, for example, adhesives and coatings.

The cured product according to this embodiment (the cured product of the composition) can be formed under the same conditions as those for the foregoing cured product (the cured product of the active ester compound).

EXAMPLES

While the present invention will be described below using examples, the present invention is not limited to the description of these examples.

Example 1

Into a flask equipped with a thermometer, a dropping funnel, a condenser, a fractionating column, and a stirrer, 268 g (2.0 mol) of o-allylphenol and 1,200 g of toluene were charged. The system was reduced in pressure and filled with nitrogen. Next, 203 g (1.0 mol) of isophthaloyl chloride was added thereto. The system was reduced in pressure and filled with nitrogen. Then 0.6 g of tetrabutylammonium bromide was added thereto. The system was controlled to 60° C. or lower while nitrogen gas purge treatment was performed, and 412 g of a 20% aqueous solution of sodium hydroxide was added dropwise thereto over a period of 3 hours. After the dropwise addition, the mixture was stirred for 1.0 hour. After completion of the reaction, the mixture was allowed to stand. Liquid separation was performed to remove the aqueous layer. Water was added to the resulting toluene layer. The mixture was stirred for 15 minutes and then allowed to stand. Liquid separation was performed to remove the aqueous layer. This operation was repeated until the pH of the aqueous layer reached 7. Drying was performed by heating under reduced pressure to provide an active ester compound represented by the following chemical formula.

[Chem. 12]

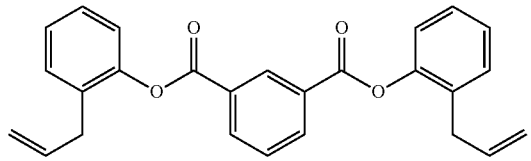

The ester equivalent of the resulting active ester compound was calculated from the feed ratio. The ester equivalent of the active ester compound was found to be 199 g/equivalent (eq.).

The E-type viscosity (25° C.) of the active ester compound was measured. As a result, the E-type viscosity (25° C.) of the active ester compound was 6,000 mPa·s.

Example 2

An active ester compound represented by the following chemical formula was prepared in the same method as in Example 1, except that 328 g (2.0 mol) of eugenol was used in place of o-allylphenol.

[Chem. 13]

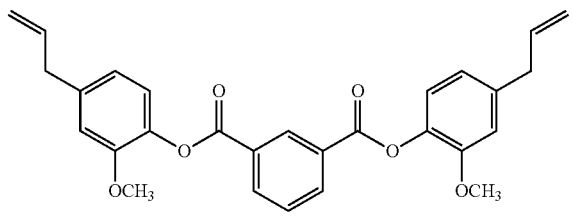

The ester equivalent of the active ester compound was calculated in the same method as in Example 1 and found to be 229 g/equivalent (eq.).

The melting point of the active ester compound was measured with a differential scanning calorimeter (DSC) at a rate of temperature increase of 3° C./min. As a result, the melting point of the active ester compound was found to be 133° C.

Example 3

An active ester compound represented by the following chemical formula was prepared in the same method as in Example 1, except that 328 g (2.0 mol) of isoeugenol was used in place of o-allylphenol.

[Chem. 14]

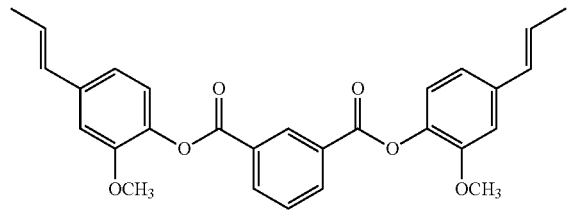

The ester equivalent of the active ester compound was calculated in the same method as in Example 1 and found to be 229 g/equivalent (eq.).

The melting point of the active ester compound was measured in the same method as in Example 2 and found to be 166° C.

Example 4

(Preparation of Allylnaphthol)

Into a flask equipped with a thermometer, a dropping funnel, a condenser, a fractionating column, and a stirrer, 144 g (1.0 mol) of 1-naphthol, 200 g of toluene, and 240 g (1.2 mol) of a 20% aqueous solution of sodium hydroxide were charged. The resulting solution was heated to 80° C. with stirring, and 92 g (1.2 mol) of allyl chloride was added dropwise thereto over a period of 3 hours. After completion of the reaction, the mixture was washed three times with 200 g of water each time. Toluene and so forth were evaporated by heating under reduced pressure to provide an allylnaphthol compound.

The hydroxyl equivalent of the resulting allylnaphthol was measured by an acetylation method. As a result, the hydroxyl equivalent of the allylnaphthol compound was found to be 195 g/equivalent (eq.).

The resulting allylnaphthol was represented by the following chemical formula.

[Chem. 15]

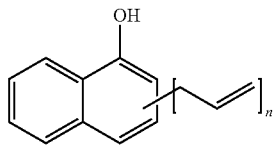

In the chemical formula, n is an integer of 0, 1, or 2, and the average value of n was 1.

(Active Ester Compound)

An active ester compound represented by the following chemical formula was prepared in the same method as in Example 1, except that 390 g (2.0 mol) of allylnaphthol prepared above was used in place of o-allylphenol.

[Chem. 16]

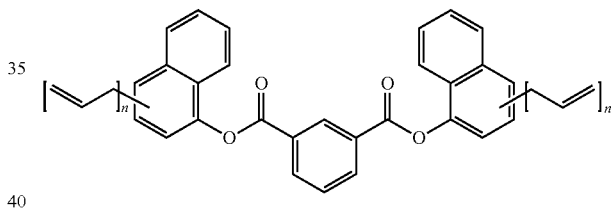

In the chemical formula, n is an integer of 0, 1, or 2, and the average value of n was 1.

The ester equivalent of the active ester compound was calculated in the same method as in Example 1 and found to be 260 g/equivalent (eq.).

The softening point of the active ester compound was measured by a B & R method. As a result, the softening point of the active ester compound was found to be 62° C.

Example 5

An active ester compound represented by the following chemical formula was prepared in the same method as in Example 1, except that 601 g (2.0 mol) of cardanol was used in place of o-allylphenol.

[Chem. 17]

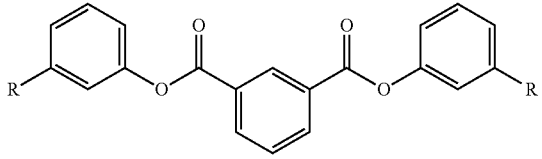

Here, each R is a mixture of —$C_{15}H_{31}$ (alkyl), —$CH_{14}$—CH=CH—$C_6H_{13}$ (monoene), —$C_7H_{14}$—CH=CH—$CH_2$—CH=CH—$C_3H_7$ (diene), and —$C_7H_{14}$—CH=CH—$CH_2$—CH=CH—$CH_2$—CH=$CH_2$ (triene) (alkyl:monoene:diene:triene=5:35:20:40). In this case, the double bonds of the monoene, the diene, and the triene have the cis-configuration.

The ester equivalent of the active ester compound and the E-type viscosity (25° C.) of the active ester compound were measured in the same method as in Example 1 and found to be 365 g/equivalent (eq.) and 430 mPa·s, respectively.

Example 6

Into a flask equipped with a thermometer, a dropping funnel, a condenser, a fractionating column, and a stirrer, 403 g (3.0 mol) of o-allylphenol and 1,200 g of toluene were charged. The system was reduced in pressure and filled with nitrogen. Next, 265 parts by mass (1.0 mol) of 1,3,5-benzenetricarbonyl trichloride was added thereto. The system was reduced in pressure and filled with nitrogen. Then 0.6 g of tetrabutylammonium bromide was added thereto. The system was controlled to 60° C. or lower while nitrogen gas purge treatment was performed, 618 g of a 20% aqueous solution of sodium hydroxide was added dropwise thereto over a period of 3 hours. After the dropwise addition, the mixture was stirred for 1.0 hour. After completion of the reaction, purification was performed in the same way as in Example 1 to give an active ester compound represented by the following chemical formula.

[Chem. 18]

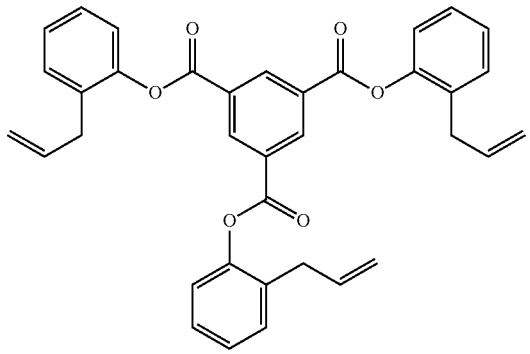

The ester equivalent of the active ester compound was measured in the same method as in Example 1 and found to be 186 g/equivalent (eq.).

The melting point of the active ester compound was measured in the same method as in Example 2 and found to be 133° C.

Comparative Example 1

Into a flask equipped with a thermometer, a dropping funnel, a condenser, a fractionating column, and a stirrer, 165 g (1 mol) of a resin (hydroxyl equivalent: 165 g/eq, softening point: 85° C.) obtained by the polyaddition reaction of dicyclopentadiene and phenol, 72 g (0.5 mol) of 1-naphthol, and 630 g of toluene were charged. The system was reduced in pressure and filled with nitrogen. Next, 152 g (0.75 mol) of isophthaloyl chloride was added thereto. The system was reduced in pressure and filled with nitrogen. Then 0.6 g of tetrabutylammonium bromide was added thereto. The system was controlled to 60° C. or lower while nitrogen gas purge treatment was performed, and 315 g of a 20% aqueous solution of sodium hydroxide was added dropwise thereto over a period of 3 hours. After the dropwise addition, the mixture was stirred for 1.0 hour. After completion of the reaction, purification was performed in the same way as in Example 1 to give a product containing an active ester compound represented by the following chemical formula.

[Chem. 19]

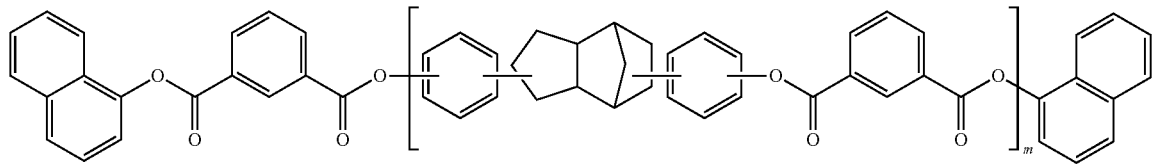

In this case, the average value of m is 2.

The ester equivalent of the active ester compound was calculated in the same method as in Example 1 and found to be 223 g/equivalent (eq.).

The softening point of the active ester compound was measured in the same method as in Example 4 and found to be 150° C.

[Evaluation]

The heat resistance and the dielectric loss tangents of the active ester compounds produced in Examples 1 to 5 and Comparative example 1 were evaluated.

(Preparation of Evaluation Sample)

Compositions 1 to 8 were produced according to proportions described in Table 1 below. As an epoxy resin, HP-7200H (dicyclopentadiene phenol-type epoxy resin, epoxy equivalent: 277 g/equivalent (eq.), available from DIC Corporation) was used. As a curing catalyst, dimethylaminopyridine (DMAP) was used. Numbers in the table are based on mass.

TABLE 1

| | Active ester compound | | Amount of epoxy resin used | Amount of curing catalyst used |
|---|---|---|---|---|
| | Type | Amount used | | |
| Composition 1 | Example 1 | 41.8 | 58.2 | 0.5 |
| Composition 2 | Example 1 | 51.9 | 48.1 | 0.5 |
| Composition 3 | Example 2 | 45.3 | 54.7 | 0.5 |
| Composition 4 | Example 3 | 45.3 | 54.7 | 0.5 |
| Composition 5 | Example 4 | 48.4 | 51.6 | 0.5 |
| Composition 6 | Example 5 | 56.9 | 43.1 | 0.5 |

TABLE 1-continued

| | Active ester compound | Amount of epoxy resin used | Amount of curing catalyst used |
|---|---|---|---|
| | Type | Amount used | | |
| Composition 7 | Example 6 | 40.2 | 59.8 | 0.5 |
| Composition 8 | Comparative example 1 | 44.6 | 55.4 | 0.5 |

Each of the resulting compositions 1 to 8 was poured into a mold (11 cm×9 cm×2.4 mm) and heated at 180° C. for 20 minutes with a press. The resulting molded article was removed from the mold and cured at 175° C. for 5 hours and then 250° C. for 2 hours. Thereby, cured products 1 to 8 (evaluation samples) were produced.

(Heat Resistance)

Each evaluation sample (thickness: 2.4 mm) was cut into a test piece having a width of 5 mm and a length of 54 mm. The test piece was subjected to dynamic mechanical analysis (DMA) using a rectangular tension method with an RSA II solid viscoelasticity measuring instrument (available from Rheometric Scientific) to measure a temperature at the point of change in elastic modulus (a large rate of change of tan δ). When multiple points of change in elastic modulus were measured, the highest temperature was evaluated as heat resistance. The measurement was performed at a frequency of 1 Hz and a rate of temperature increase of 3° C./min. Table 2 presents the results.

(Dielectric Loss Tangent)

The dielectric loss tangent was measured by a resonant cavity method with an E8362C network analyzer (available from Agilent Technologies, Inc). Specifically, each evaluation sample was dried by heating in vacuum at 105° C. for 2 hours and stored in a room at a temperature of 23° C. and a humidity of 50% for 24 hours, and then the dielectric loss tangent thereof was measured at 1 GHz. Table 2 presents the results.

TABLE 2

| | Active ester compound | Heat resistance (° C.) | Dielectric loss tangent |
|---|---|---|---|
| Cured product 1 | Example 1 | 249 | 0.0057 |
| Cured product 2 | Example 1 | 245 | 0.0044 |
| Cured product 3 | Example 2 | 257 | 0.0075 |
| Cured product 4 | Example 3 | 235 | 0.0073 |
| Cured product 5 | Example 4 | 250 | 0.0047 |
| Cured product 6 | Example 5 | 195 | 0.0075 |
| Cured product 7 | Example 6 | 275 | 0.0060 |
| Cured product 8 | Comparative example 1 | 180 | 0.0080 |

The results presented in Table 2 indicate that the cured products 1 to 7 using the active ester compounds of Examples 1 to 6 have higher heat resistance than the cured product 8 using the active ester compound of Comparative example 1. It is also found that the cured products 1 to 7 have lower dielectric loss tangents than cured product 8.

The invention claimed is:

1. A composition, comprising the active ester compound and an epoxy resin,
wherein the mass ratio of the amount of the active ester compound used to the amount of the epoxy resin used (active ester compound/epoxy resin) is 1.1 to 5.0;
wherein the active ester compound is represented by chemical formula (1):

[Chem. 1]

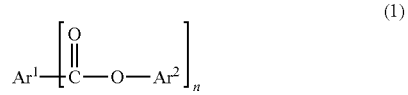

where in chemical formula (1),
Ar$^1$ is a substituted or unsubstituted first aromatic ring group; and
each Ar$^2$ is independently a substituted or unsubstituted second aromatic ring phenyl or naphthyl group having one alkenyl group substituent having 2 to 15 carbon atoms and, optionally, one or more substituents chosen from the group consisting of an alkyl group having 1 to 10 carbon atoms, an alkoxy group having 1 to 10 carbon atoms, an alkyloxycarbonyl group having 2 to 15 carbon atoms, an alkylcarbonyloxy group having 2 to 15 carbon atoms, and a halogen atom, wherein at least one of Ar$^1$ and Ar$^2$ has an unsaturated bond-containing substituent,
and n is an integer of 2 or 3;
and wherein the epoxy resin includes a phenol novolac epoxy resin, an aralkyl epoxy resin, a bisphenol epoxy resin, a biphenyl epoxy resin, a naphthalene epoxy resin, a binaphthol epoxy resin; a binaphthyl epoxy resin; a dicyclopentadiene epoxy resin, a glycidylamine epoxy resin, a diglycidyl ester resin, or a benzopyran epoxy resin.

2. A cured product obtained by curing the composition according to claim 1.

3. A printed circuit board obtained using the composition according to claim 1.

4. A semiconductor sealing material obtained using the composition according to claim 1.

5. A build-up film obtained using the composition according to claim 1.

6. The composition of claim 1 wherein, in the active ester compound, the unsaturated bond-containing alkenyl group substituent is an alkenyl group having 2 to 5 carbon atoms.

7. The composition of claim 1 wherein, in the active ester compound, the unsaturated bond-containing alkenyl group substituent is attached to an ortho-position with respect to a position of Ar$^2$ to which an oxygen atom is bonded.

8. The composition of claim 1 wherein, in the active ester compound,
Ar$^1$ is a substituted or unsubstituted first aromatic hydrocarbon group having 6 to 30 carbon atoms, and
each Ar$^2$ is a substituted or unsubstituted second aromatic hydrocarbon group having 6 to 30 carbon atoms.

9. The composition of claim 1 wherein the epoxy resin is cresol novolac epoxy resin, α-naphthol novolac epoxy resin, β-naphthol novolac epoxy resin, bisphenol A novolac epoxy resin, biphenyl novolac epoxy resin, phenol aralkyl epoxy resin, naphthol aralkyl epoxy resin, phenol biphenylaralkyl epoxy resin, bisphenol A epoxy resin, bisphenol AP epoxy resin, bisphenol AF epoxy resin, bisphenol B epoxy resin, bisphenol BP epoxy resin, bisphenol C epoxy resin, bisphenol E epoxy resin, bisphenol F epoxy resin, bisphenol S epoxy resin, tetrabromobisphenol A epoxy resin, biphenyl epoxy resin, tetramethylbiphenyl epoxy resin, an epoxy resin having a biphenyl skeleton, an epoxy resin having a diglycidyloxybenzene skeleton, naphthalene epoxy resin, binaphthol epoxy resin, binaphthyl epoxy resin; dicyclopentadiene phenol epoxy resin; tetraglycidyldiaminodiphenylmethane epoxy resin, triglycidyl-p-aminophenol epoxy resin, diaminodiphenyl sulfone glycidylamine epoxy resin; diglycidyl 2,6-naphthalenedicarboxylate epoxy resin, hexahydrophthalic anhydride glycidyl ester epoxy resin, dibenzopyran, hexamethyldibenzopyran, or 7-phenylhexamethyldibenzopyran.

* * * * *